US009128055B2

(12) United States Patent
Sekino et al.

(10) Patent No.: US 9,128,055 B2
(45) Date of Patent: Sep. 8, 2015

(54) INFORMATION PROCESSING APPARATUS, INFORMATION PROCESSING METHOD, PROGRAM, AND METHOD OF CORRECTING INTENSITY OF FLUORESCENCE SPECTRUM

(75) Inventors: Masashi Sekino, Tokyo (JP); Yasunobu Kato, Kanagawa (JP); Tatsumi Ito, Kanagawa (JP)

(73) Assignee: Sony Corporation, Tokyo (JP)

( * ) Notice: Subject to any disclaimer, the term of this patent is extended or adjusted under 35 U.S.C. 154(b) by 528 days.

(21) Appl. No.: 13/550,639

(22) Filed: Jul. 17, 2012

(65) Prior Publication Data
US 2013/0026391 A1 Jan. 31, 2013

(30) Foreign Application Priority Data

Jul. 25, 2011 (JP) .................................. 2011-161758

(51) Int. Cl.
*G06F 17/18* (2006.01)
*G01J 3/02* (2006.01)
*G01N 21/64* (2006.01)

(52) U.S. Cl.
CPC ........ *G01N 21/6428* (2013.01); *G01N 21/6408* (2013.01); *G01N 21/6458* (2013.01)

(58) Field of Classification Search
CPC ............ G01N 21/18; G06F 17/18; G01J 3/02
USPC ................. 702/181; 356/600, 601; 250/459.1
See application file for complete search history.

(56) References Cited

U.S. PATENT DOCUMENTS

| 5,237,515 | A | 8/1993 | Herron et al. |
| 6,015,667 | A | 1/2000 | Sharaf |
| 6,174,291 | B1 * | 1/2001 | McMahon et al. ............ 600/564 |
| 7,006,235 | B2 * | 2/2006 | Levy et al. .................... 356/600 |

(Continued)

FOREIGN PATENT DOCUMENTS

| CN | 101193185 B | * | 7/2010 |
| DE | 19915137 A1 | | 10/2000 |

(Continued)

OTHER PUBLICATIONS

Steinborn et al., TRLFS: analysing spectra with an expectation-maximization (EM) algorithm. Spectrochim Acta A Mol Biomol Spectrosc. Dec. 15, 2008;71(4):1425-32. Epub May 2, 2008.
Suárez Araujo et al., HUMANN-based system to identify benzimidazole fungicides using multi-synchronous fluorescence spectra: an ensemble approach. Anal Bioanal Chem. Jun. 2009;394(4):1059-72. Epub Mar. 6, 2009.

(Continued)

*Primary Examiner* — Carol S Tsai
(74) *Attorney, Agent, or Firm* — Wolf, Greenfield & Sacks, P.C.

(57) ABSTRACT

Provided is an information processing apparatus including an estimation unit that expresses a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, models the light intensity distribution obtained from each of the reference measurement objects so as to follow a predetermined probability distribution, and estimates a combination coefficient of the linear combination from the light intensity distribution obtained from the measurement object of the measurement target.

10 Claims, 26 Drawing Sheets

(56) References Cited

U.S. PATENT DOCUMENTS

| | | | |
|---|---|---|---|
| 7,646,002 B2* | 1/2010 | Sendai | 250/461.2 |
| 8,582,124 B2* | 11/2013 | Yamazaki et al. | 356/630 |
| 2003/0020908 A1 | 1/2003 | Frost et al. | |
| 2006/0247535 A1* | 11/2006 | Sendai | 600/476 |
| 2008/0212866 A1* | 9/2008 | Lett et al. | 382/133 |
| 2013/0038883 A1* | 2/2013 | Yamazaki et al. | 356/630 |
| 2013/0107256 A1* | 5/2013 | Mitsuyama et al. | 356/343 |

FOREIGN PATENT DOCUMENTS

| | | |
|---|---|---|
| JP | 2000-503774 A | 3/2000 |
| JP | 2003-083894 A | 3/2003 |

OTHER PUBLICATIONS

Djikanovic et al., Deconvolution of fluorescence spectra: Contribution to the structure analysis of complex molecules, Colloids and Surfaces B: Biointerfaces, 2007, vol. 54, pp. 188-192, Available online Oct. 24-26.

Gallie et al., Technical Note, Equivalence of modified Gaussian model (MGM) in wavenumber and Gaussian in wavelength for deconvolution of hyperspectral reflectance spectra, International Journal of Remote Sensing, vol. 29, No. 14, Jul. 20, 2008, pp. 4089-4096.

Re'Vay Z., Analysis of the Probability Distribution Method for Spectrum Decomposition, Mikrochimica Acta, 1997, vol. 126, No. 1-2, pp. 77-81.

* cited by examiner

INTENSITY CORRECTION IN ACCORDANCE WITH INVERSE MATRIX METHOD

INTENSITY CORRECTION IN ACCORDANCE WITH RESTRICTED LEAST SQUARE METHOD

1: INFORMATION PROCESSING SYSTEM

FLOW OF MEASUREMENT SAMPLE

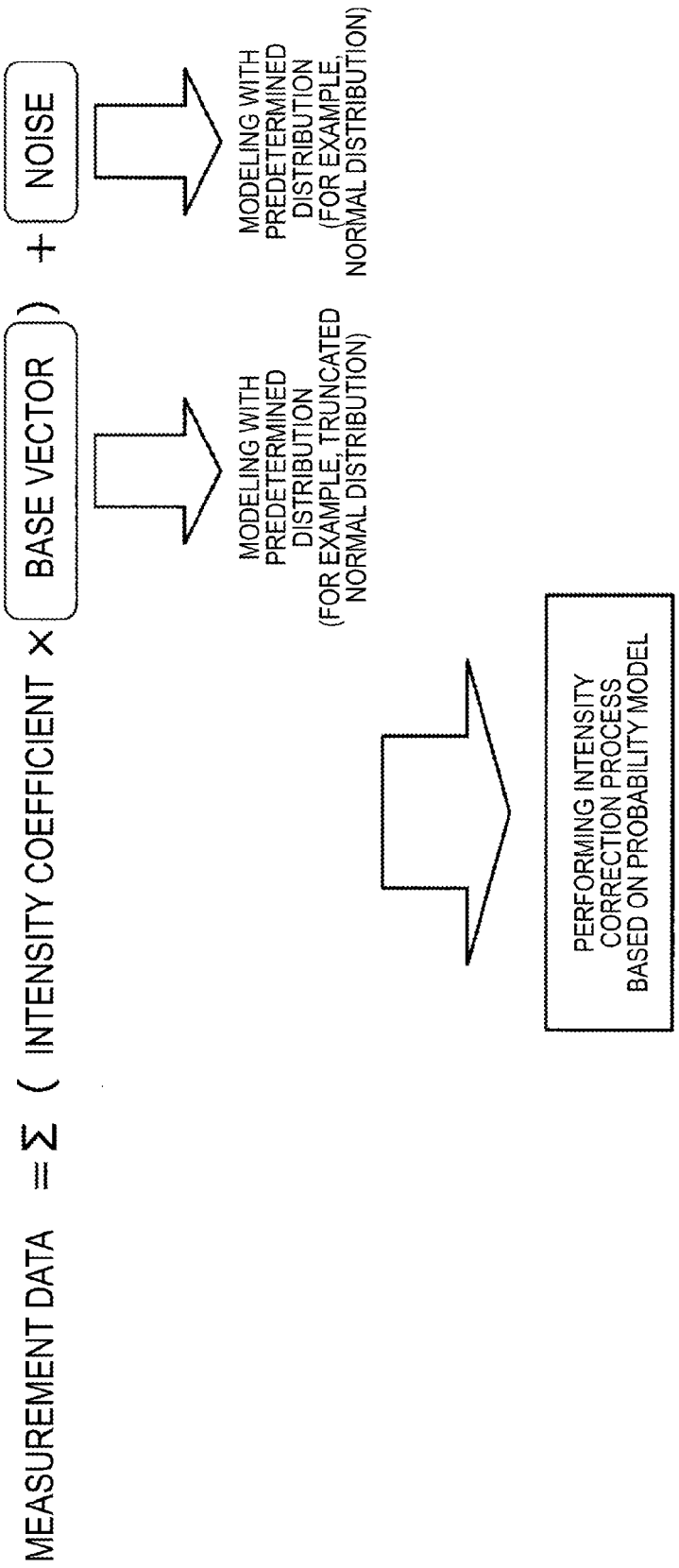

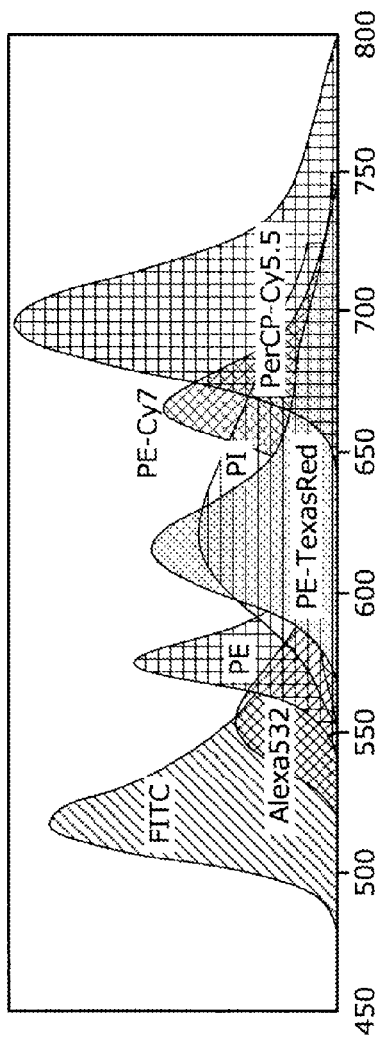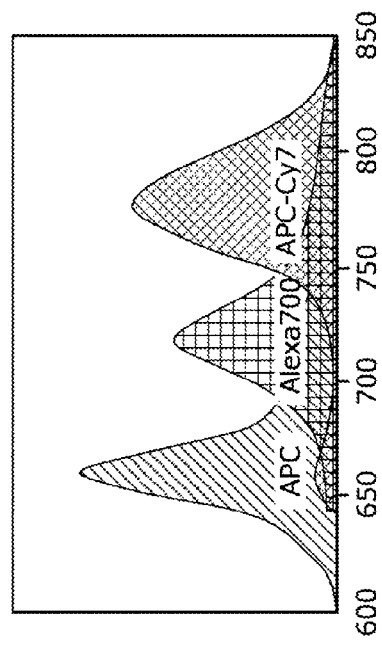
FIG. 15

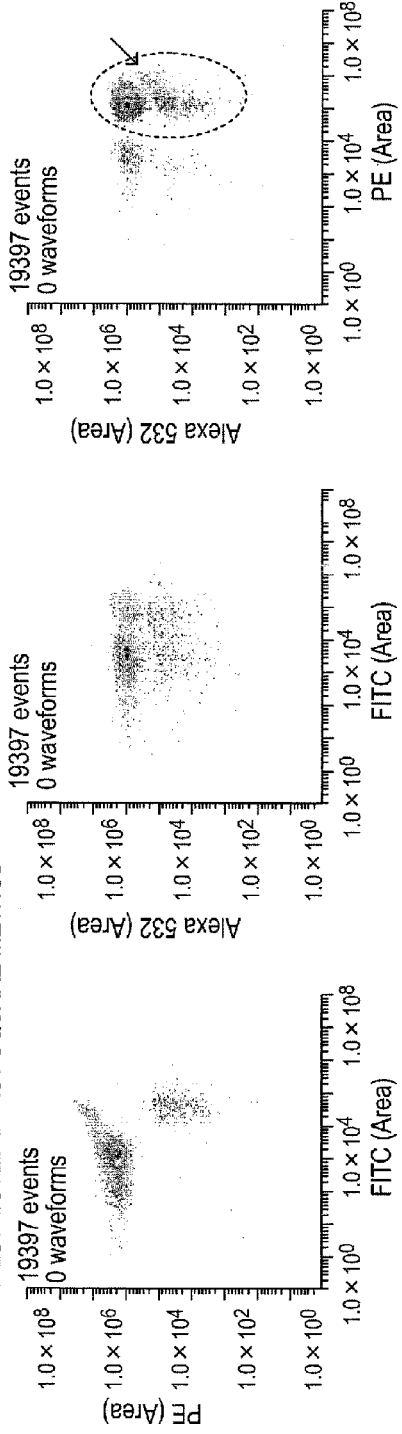
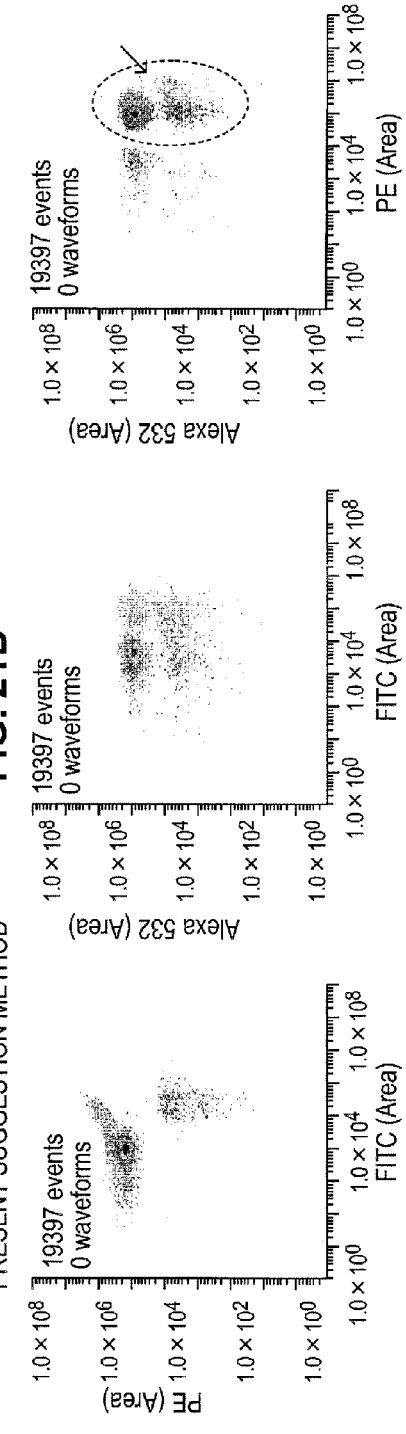
FIG. 21A RESTRICTED LEAST SQUARE METHOD
FIG. 21B PRESENT SUGGESTION METHOD

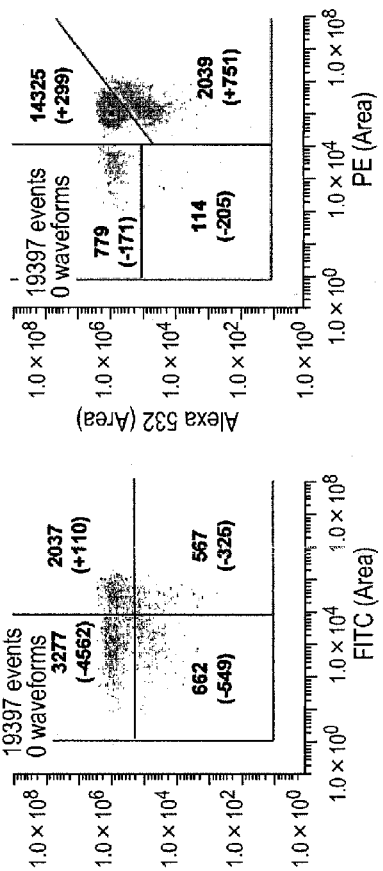
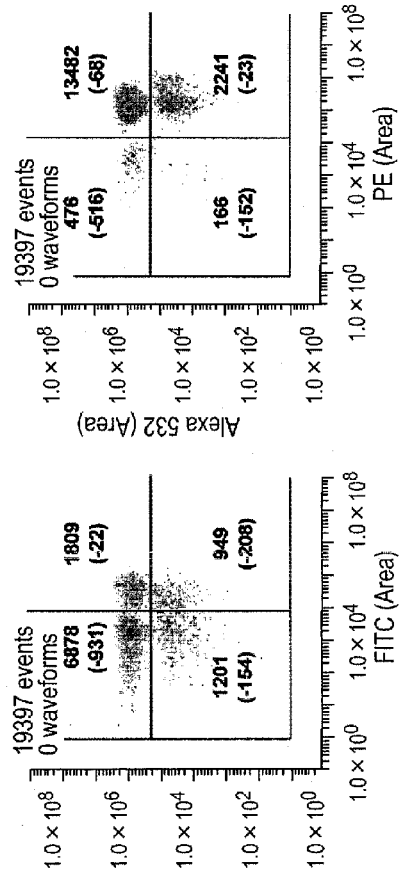
FIG. 23A
FIG. 23B

INFORMATION PROCESSING APPARATUS, INFORMATION PROCESSING METHOD, PROGRAM, AND METHOD OF CORRECTING INTENSITY OF FLUORESCENCE SPECTRUM

BACKGROUND

The present disclosure relates to an information processing apparatus, an information processing method, a program, and a method of correcting the intensity of a fluorescence spectrum.

To measure the characteristics of microparticles such as cells, an apparatus (for example, a flow cytometer) that irradiates a laser beam to microparticles marked by a fluorescent pigment and measures the intensity or a pattern of fluorescence coming from the excited fluorescent pigment is used. As a technology for analyzing the characteristics of microparticles in further detail, a technology, called multi-color measurement, of marking microparticles using a plurality of fluorescent pigments and measuring fluorescence coming from each fluorescent pigment radiated with a laser beam using optical detectors with different light reception wavelength bands has also been used. Further, a transparent wavelength band of an optical filter provided in each optical detector to restrict the light reception wavelength band is designed in accordance with the fluorescent wavelength of the fluorescence coming from the fluorescent pigment to be measured.

For example, fluorescein isothiocyanate (FITC) or phycoerythrin (PE) is used as the fluorescent pigment. When a fluorescence spectrum obtained by irradiating a laser beam to microparticles marked with such a fluorescent pigment is measured, the presence of the fluorescence wavelength bands overlapping one another is confirmed. That is, even when the fluorescence obtained by irradiating the laser beam to the microparticles is separated in accordance with wavelength bands by an optical filter in the multi-color measurement, a fluorescent component coming from a fluorescent pigment other than a target fluorescent component is considered to leak in the fluorescence spectrum detected by each optical detector. When the leakage of the fluorescence occurs, a deviation may occur between a fluorescence intensity measured by each optical detector and the fluorescence intensity of the fluorescence actually coming from the target fluorescent pigment. As a result, a measurement error occurs.

To correct such a measurement error, a fluorescence correction process (compensation) of subtracting the fluorescence intensity corresponding to the leakage of the fluorescence from the fluorescence intensity measured by the optical detector is performed. The fluorescence correction process is a process of performing correction (hereinafter referred to as fluorescence correction) on the measured fluorescence intensity such that the fluorescence intensity measured by the optical detector approximates the fluorescence intensity of the fluorescence actually coming from the target fluorescent pigment. For example, as a method of performing the fluorescence correction, Japanese Unexamined Patent Application Publication No. 2003-83894 discloses a method of mathematically correcting a fluorescence intensity.

According to the method disclosed in Japanese Unexamined Patent Application Publication No. 2003-83894, the fluorescence intensity of the fluorescence actually coming from the target fluorescent pigment is calculated using a vector which has a fluorescence intensity (detection value) measured by each optical detector as a component and applying an inverse matrix of a correction matrix set in advance in the vector. The correction matrix is also called a leakage matrix. The correction matrix is a matrix which is prepared by analyzing a fluorescence wavelength distribution of microparticles singly marked with respective fluorescent pigments and arranging the fluorescence wavelength distributions of each fluorescent pigments as a row vector.

SUMMARY

In the fluorescence correction process disclosed in Japanese Unexamined Patent Application Publication No. 2003-83894, a negative value is allowed as the value of a matrix component of the correction matrix. For this reason, when the fluorescence correction process is applied, the corrected fluorescence intensity has a negative value in some cases. The reason that the corrected fluorescence intensity has a negative value is that noise contained in a detection value of each optical detector affects the value of each matrix component. In effect, however, the fluorescence intensity does not intrinsically have a negative value. Further, the fact that the calculated fluorescence intensity of the fluorescence coming from a given fluorescent pigment has a negative value means that an error occurs in the positive direction in the fluorescence intensity of another fluorescent pigment at the same time.

A sub-group (hereinafter referred to as a sub-population) in which the fluorescence intensity of a given fluorescent pigment has a negative value is considered to be present in a microparticle group (hereinafter referred to as a population) to be analyzed. In this case, when a two-dimensional correlation diagram (hereinafter referred to as a cytogram) in which the fluorescence intensity of the given fluorescent pigment is plotted in a logarithmic scale is generated, the sub-population may not be plotted on the cytogram. Therefore, there is a concern that a user may misunderstand that the population plotted on the cytogram is smaller than an actual population.

In the fluorescence correction process disclosed in Japanese Unexamined Patent Application Publication No. 2003-83894, an average value of the autofluorescence intensities of the entire population is used for calculation when the detection value of autofluorescence coming from microparticles is subtracted as a background from the detection value of each optical detector. However, the intensity or pattern of the autofluorescence is different in each sub-population. For this reason, the calculation itself in which the average value is subtracted uniformly for all of the sub-populations causes an error of the calculation value of the fluorescence intensity. In particular, when the autofluorescence intensity is irregular among the sub-populations to be analyzed, the error may be considerable.

Here, a situation in which a peak present in a given wavelength band originates from a plurality of chemical species in the measured fluorescence spectrum does not occur only due to the fluorescence spectrum of the microparticles marked by the above-described fluorescent pigments. The situation in which a given peak originates from a plurality of chemical species in the measured fluorescence spectrum can also occur even in an emission spectrum, an absorption spectrum, or the like in which the plurality of chemical species coexist. That is, in a process of analyzing the spectrum of light coming from a plurality of light emission components for each light emission component, it is necessary to perform a correction method of effectively suppressing an element of another light emission component leaking to the spectrum of the light coming from a target light emission component.

It is desirable to provide an information processing apparatus, an information processing method, a program, and a method of correcting the intensity of a fluorescence spectrum, which are capable of extracting a target spectrum component from a measured spectrum with higher accuracy.

According to an embodiment of the present disclosure, there is provided an information processing apparatus including: an estimation unit that expresses a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, models the light intensity distribution obtained from each of the reference measurement objects so as to follow a predetermined probability distribution, and estimates a combination coefficient of the linear combination from the light intensity distribution obtained from the measurement object of the measurement target.

According to another embodiment of the present disclosure, there is provided an information processing method including: expressing a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, modeling the light intensity distribution obtained from each of the reference measurement objects so as to follow a predetermined probability distribution, and estimating a combination coefficient of the linear combination from the light intensity distribution obtained from the measurement object of the measurement target.

According to another embodiment of the present disclosure, there is provided a program for causing a computer to execute a function of: expressing a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, modeling the light intensity distribution obtained from each reference measurement object so as to follow a predetermined probability distribution, and estimating a combination coefficient of the linear combination from the light intensity distribution obtained from the measurement object of the measurement target.

According to another embodiment of the present disclosure, there is provided a method of correcting an intensity of a fluorescence spectrum, including: measuring a fluorescence spectrum of microparticles by irradiating light with predetermined wavelength to the microparticles which are multi-dyed with a plurality of fluorescent pigments; and correcting a fluorescent intensity of the measured fluorescent spectrum of the microparticles based on information regarding fluorescence characteristics of the single fluorescent pigment, wherein, to correct the fluorescent intensity, the fluorescence spectrum of the microparticles is treated as a linear sum of multiplications of fluorescence spectra of the fluorescent pigments and predetermined weighting coefficients, and a parameter indicating an intensity distribution corresponding to the fluorescence spectrum of the fluorescent pigment is set based on the information regarding the fluorescence characteristics of the single fluorescent pigment, a likely weighting coefficient corresponding to the fluorescence spectrum of the microparticles and the parameter indicating the intensity distribution are estimated based on the fluorescent spectrum of the microparticles and the intensity distribution corresponding to the fluorescence spectrum of the fluorescent pigment, and the estimated weighting coefficient is considered as a fluorescence intensity originating from each fluorescent pigment.

According to an embodiment of the present disclosure, a parameter setting control unit treats a fluorescence spectrum measured by irradiating light with a predetermined wavelength to a measurement object as a linear sum of multiplications of reference fluorescence spectra originating from a single or a plurality of spectra and predetermined weighting coefficients and sets a parameter indicating an intensity distribution corresponding to the reference spectrum. An estimation unit estimates a likely weighting coefficient corresponding to the spectrum of the measurement object and the parameter indicating the intensity distribution based on the spectrum of the measurement spectrum and the intensity distribution corresponding to the reference spectrum. An output unit outputs the estimated weighting coefficient as a fluorescence intensity originating from each reference spectrum.

According to the embodiment of the present disclosure described above, it is possible to extract the target spectrum component from the measured spectrum with higher accuracy.

BRIEF DESCRIPTION OF THE DRAWINGS

FIG. 7 is a diagram schematically illustrating the intensity correction process according to the first embodiment;

FIG. 15 is a diagram illustrating a base vector generation process using the information processing method according to the first embodiment;

FIGS. 21A and 21B are graphs illustrating two-dimensional correlation diagrams of a mixture sample;

FIGS. 23A and 23B are graphs illustrating three-dimensional correlation diagrams of the mixture sample.

DETAILED DESCRIPTION OF THE EMBODIMENTS

Figure 1:
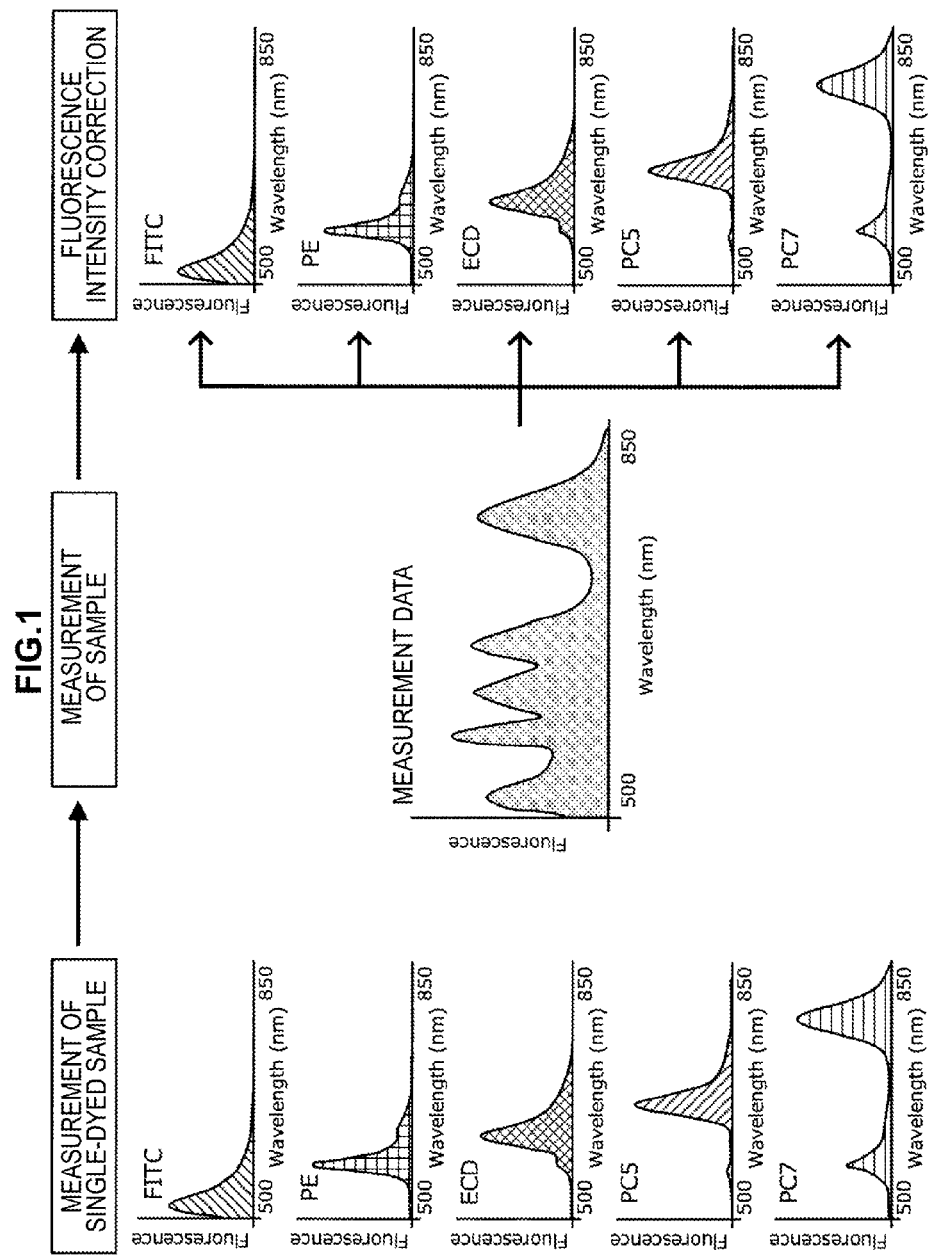
FIG. 1 is a diagram illustrating a fluorescence intensity correction process.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be made in the following order.
(1) Technology forming Basis of Technical Spirit of the Present Disclosure
(2) First Embodiment
 (2-1) Information Processing System
 (2-2) Configuration of Information Processing Apparatus
 (2-3) Flow of Information Processing Method
 (2-4) Example of Flow of Fluorescence Intensity Correction Method
(3) Hardware Configuration of Information Processing Apparatus according to Embodiment of the Present Disclosure
(4) Examples
(Technology as Basis of Technical Spirit of the Present Disclosure)

First, before an information processing apparatus and an information processing method according to an embodiment of the present disclosure are described, a technology (hereinafter referred to as a basis technology) forming a basis of the technical spirit of the present disclosure will be described simply with reference to FIGS. 1 to 4. FIGS. 1 to 4 are diagrams illustrating a fluorescence intensity correction process.

For example, a fluorescence intensity correction process performed on a fluorescence spectrum of biological cells or the like marked with fluorescent pigments, which is measured by a flow cytometer, will be described below.

A case in which microparticles such as biological cells are multi-dyed with plural kinds of fluorescent pigments and the fluorescence spectrum of the dyed microparticles is measured will be considered.

First, a single-dyed sample in which microparticles are dyed singly with each fluorescent pigment is prepared. Then, as shown in FIG. 1, the fluorescence spectrum of the single-dyed sample is measured in advance. In the example shown in FIG. 1, when five kinds of fluorescent pigments, FITC, PE, ECD, PC5, and PC7, are singly used, the fluorescence spectra of the fluorescent pigments are measured in advance. Thereafter, a sample is multi-dyed with the plural kinds of fluorescent pigments and a fluorescence spectrum is measured. The measured fluorescence spectrum is a spectrum in which the fluorescence intensities originating from the respective fluorescent pigments used to mark the microparticles overlap. Therefore, by performing the fluorescence intensity correction process on the fluorescence spectrum obtained through the measurement, the degree to which the fluorescence intensity originating from a given fluorescent pigment overlaps the other fluorescence intensities is specified.

Here, a method (hereinafter, also referred to as an inverse matrix method) using the correction matrix disclosed in Japanese Unexamined Patent Application Publication No. 2003-83894 will be introduced. This method is used to calculate a genuine fluorescence intensity (FL) by applying the inverse matrix of the correction matrix to the fluorescence intensity (MI) obtained by each optical detector as the measurement result, as in Equation 11 below.

$$\begin{pmatrix} FL_1 \\ FL_2 \\ FL_3 \\ FL_4 \\ FL_5 \end{pmatrix} = \begin{pmatrix} a_{11} & a_{21} & a_{31} & a_{41} & a_{51} \\ a_{12} & a_{22} & a_{32} & a_{42} & a_{52} \\ a_{13} & a_{23} & a_{33} & a_{43} & a_{53} \\ a_{14} & a_{24} & a_{34} & a_{44} & a_{54} \\ a_{15} & a_{25} & a_{35} & a_{45} & a_{55} \end{pmatrix}^{-1} \begin{pmatrix} MI_1 \\ MI_2 \\ MI_3 \\ MI_4 \\ MI_5 \end{pmatrix} \quad \text{(Equation 11)}$$

Figure 2:
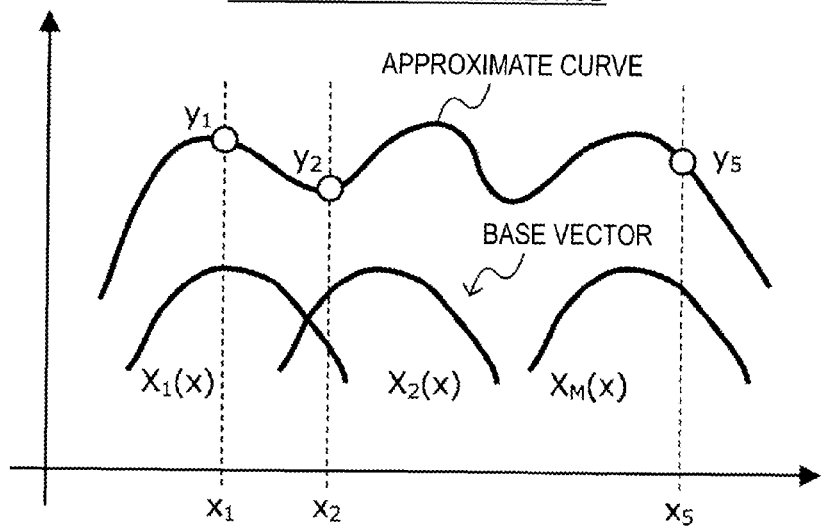
FIG. 2 is a diagram illustrating the fluorescence intensity correction process.

FIG. 2 is a diagram schematically illustrating the fluorescence intensity correction process in accordance with the inverse matrix method. The fluorescence intensity correction process in accordance with the inverse matrix method can also be said to be a process of calculating an approximate curve passing through the measurement data measured by the respective optical detectors above base vectors which are the fluorescence spectra of the superimposed fluorescent pigments. That is, on the assumption that $y_1$ to $y_5$ are the measurement data of optical detectors $x_1$ to $x_5$ and $X_1(x)$ to $X_M(x)$ are base vectors, the fluorescence intensity correction process in accordance with the inverse matrix method is a process of calculating an approximate curve passing through all of the measurement data $y_1$ to $y_5$ using the base vectors $X_1(x)$ to $X_M(x)$.

In a case of the inverse matrix method, the genuine fluorescence intensity has a negative value in some cases. In the case of the inverse matrix method, it is necessary to set the number of installed optical detectors to be same as the number of fluorescent pigments to be used. Further, the condition itself that the measurement data of each optical detector is present on the approximate curve may cause an error of the calculated fluorescence intensity.

The proposers of the present disclosure have examined a method of resolving the above-mentioned problem of the inverse matrix method. As a result, the proposers of the present disclosure have not calculated an approximate curve passing through the measurement data of the optical detectors, but have devised a method of calculating a likely approximate curve estimated from the measurement data of the optical detectors in accordance with the least square method, as exemplified in FIG. 3. On the assumption that $y_1$ to $y_N$ are measurement data of optical detectors $x_1$ to $x_N$ and $X_1(x)$ to $X_M(x)$ are base vectors, this method is a method of calculating an approximate curve with the smallest error with the measurement data $y_1$ to $y_N$ using the base vectors $X_1(x)$ to $X_M(x)$.

Figure 4:
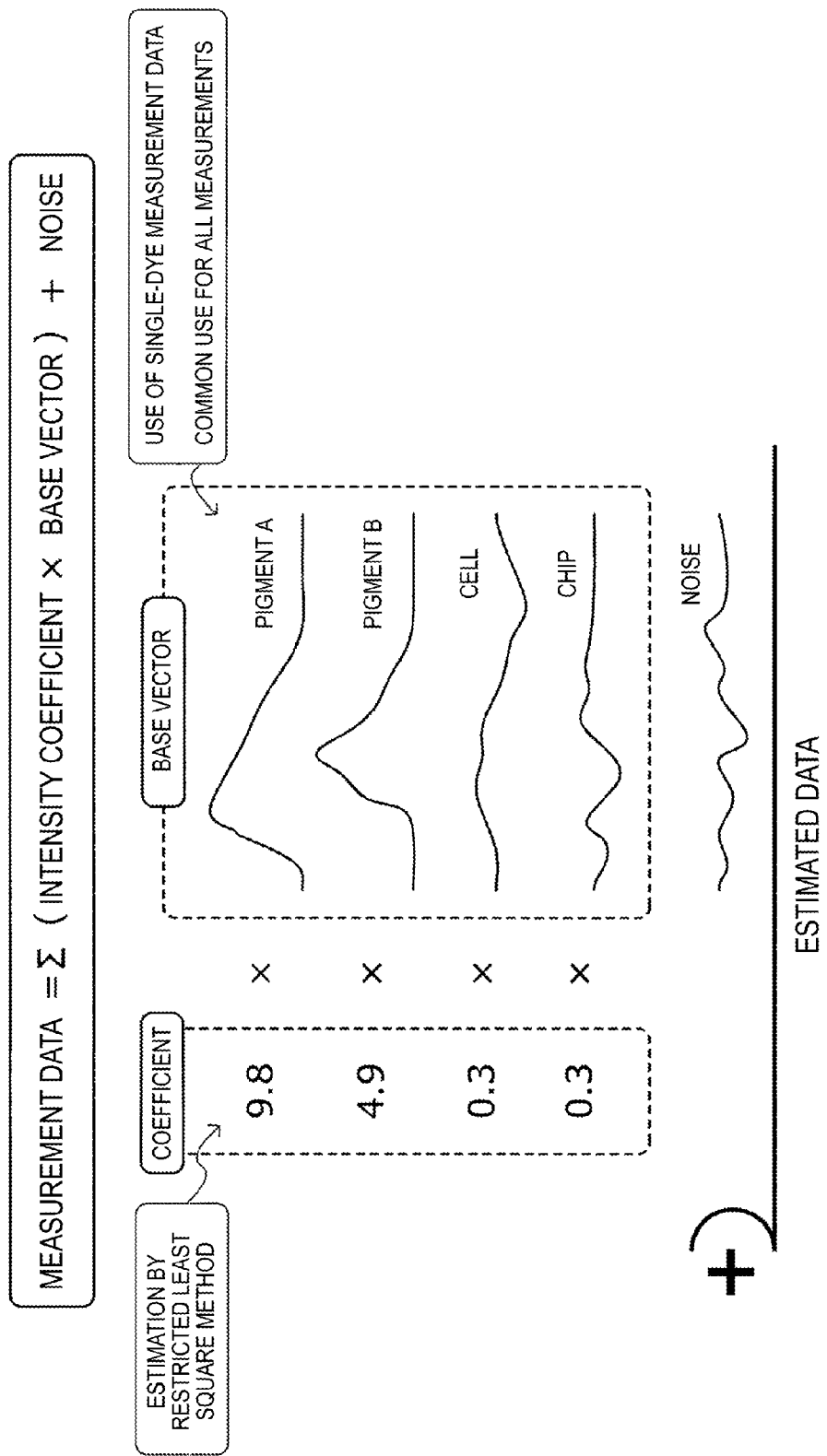
FIG. 4 is a diagram illustrating the fluorescence intensity correction process.

The fluorescence intensity correction method using the least square method can be schematically illustrated as in FIG. 4. Hereinafter, the fluorescence intensity correction method using the least square method will be described with reference to FIG. 4.

A set (that is, a fluorescence spectrum) of the measurement data measured by the optical detectors is a result obtained by superimposing noise on a linear sum of the multiplications of fluorescence spectra (for example, fluorescence spectra when a sample is dyed singly with a single fluorescent pigment or autofluorescence spectra of a sample or the like), which serve as a reference used as a base vector, and predetermined coefficients (intensity coefficients). A specific value of each intensity coefficient is determined based on the measurement data measured by each optical detector in accordance with the least square method. The intensity coefficient determined in this way is the corrected fluorescence intensity (that is, the genuine fluorescence intensity).

Here, when the least square method is performed to calculate the intensity coefficient shown in FIG. 4, the proposers of the present disclosure have formulated an idea of providing a restriction in which the value of the intensity coefficient is equal to or greater than a predetermined minimum value (for example, equal to or greater than zero). According to this idea, it is possible to resolve the defect of the inverse matrix method in which the calculated genuine fluorescence intensity has a negative value. A method of realizing the idea of the proposers of the present disclosure is referred to as a "restricted least square method" below.

Hereinafter, a method conforming to the restricted least square method will be described simply using specific equations.

First, on the assumption that $y(x)$ is a measured fluorescence spectrum, $X_k(x)$ is a base vector of a fluorescent pigment k (k=1, . . . , M), and $a_k$ is an intensity coefficient of the fluorescent pigment k, the measured fluorescence spectrum $y(x)$ is expressed by Equation 21 below. Here, on the assumption that $y_1$ is measurement data obtained by an i-th (i=1, N) optical detector, the interest least square method is ultimately a task of calculating the intensity coefficient used to provide the minimum value of an evaluation function $\chi^2$ shown in Equation 22 below. Further, in Equation 22 below, $\sigma_1$ is an inverse number of a weighting coefficient for the measurement value of the i-th optical detector. As the inverse number of the weighting coefficient, for example, a measurement error variance of the i-th optical detector may be used or 1 may be used.

$$y(x) = \sum_{k=1}^{M} a_k \cdot X_k(x) \quad \text{(Equation 21)}$$

$$\chi^2 \equiv \sum_{i=1}^{N} \left[ \frac{y_i - \sum_{k=1}^{M} a_k \cdot X_k(x_i)}{\sigma_i} \right]^2 \quad \text{(Equation 22)}$$

All known methods can be used as a method of calculating the intensity coefficient $a_k$ used to provide the minimum value of the evaluation function expressed by Equation 22.

<Method of Calculating Intensity Coefficient $a_k$—Method 1>

For example, a normal equation (matrix equation) in which the evaluation function expressed in Equation 22 has the minimum value when all of the values obtained by differentiating Equation 22 by the intensity coefficient $a_k$ are zero may be derived and the derived normal equation (actually, M simultaneous linear equations) may be solved to calculate the intensity coefficient $a_k$.

That is, the condition in which the value obtained by differentiating the right side of Equation 22 by the intensity coefficient $a_k$ is zero is expressed as in Equation 23 below. Here, in Equation 23 below, an index k is an integer of "k=1, . . . , M."

$$0 = \sum_{i=1}^{N} \frac{1}{\sigma_i^2} \left[ y_i - \sum_{j=1}^{M} a_j X_j(x_i) \right] \cdot X_k(x_i) \quad \text{(Equation 23)}$$

Here, Equation 23 above can be modified to the form of a normal equation expressed by Equation 24 below by changing the calculation order of the sum. Further, in Equation 24 below, $a_{kj}$ and $\beta_k$ are values expressed by Equation 25 and Equation 26 below, respectively.

$$\sum_{j=1}^{M} a_{kj} a_j = \beta_k \quad \text{(Equation 24)}$$

$$a_{ki} = \sum_{i=1}^{N} \frac{X_j(x_i) \cdot X_k(x_i)}{\sigma_i^2} \quad \text{(Equation 25)}$$

$$\beta_k = \sum_{i=1}^{N} \frac{y_i \cdot X_k(x_i)}{\sigma_i^2} \quad \text{(Equation 26)}$$

When an N×M matrix A with a component $A_{ij}$ expressed by Equation 27 below, an N-dimensional vector b with a component $b_i$ expressed by Equation 28 below, and an M-dimensional vector a with intensity coefficients $a_1$ to $a_M$ are considered, the normal equation expressed by Equation 24 above can be expressed as a matrix equation as in Equation 29 below.

$$A_{ij} = \frac{X_j(x_i)}{\sigma_i} \quad \text{(Equation 27)}$$

$$b_i = \frac{y_i}{\sigma_i} \quad \text{(Equation 28)}$$

$$b_i = \frac{y_i}{\sigma_i} \quad \text{(Equation 29)}$$

As apparent from Equation 24 or Equation 29, the equations are M simultaneously linear equations. By solving the equations, the intensity coefficients $a_1$ to $a_M$ can be calculated.

<Method of Calculating Intensity Coefficient $a_k$—Method 2>

An arbitrary N×M matrix X can be decomposed, as in Equation 30 below, into orthonormal matrixes U and V and a diagonal matrix W having non-negative values called singular values as diagonal components. Here, the matrix U is an N×M matrix and the matrices V and W are M×M matrices.

Equation 22, which is an evaluation function, can be expressed as Equation 22' below using the matrix A and vectors a and b.

$$X = UWV^T = U \cdot \begin{pmatrix} w_1 & & & & \\ & w_2 & & 0 & \\ & & \ddots & & \\ & 0 & & \ddots & \\ & & & & w_M \end{pmatrix} \cdot V^T \quad \text{(Equation 30)}$$

$$\chi^2 = |A \cdot a - b|^2 \quad \text{(Equation 22')}$$

Here, when the matrix A in Equation 22' is decomposed into singular values and the matrices U, W, and V can be obtained in accordance with the matrix A, the vector a used to provide the minimum value of Equation 22' can be calculated by Equation 31 below.

$$a = V \cdot \begin{pmatrix} \frac{1}{w_1} & & & & \\ & \frac{1}{w_2} & & 0 & \\ & & \ddots & & \\ & 0 & & \ddots & \\ & & & & \frac{1}{w_M} \end{pmatrix} \cdot (U^T \cdot b) = \quad \text{(Equation 31)}$$

$$V \cdot [\text{diag}(1/w_j)] \cdot (U^T \cdot b)$$

<Examination of Intensity Correction Method in Accordance with Restricted Least Square Method>

The proposers of the present disclosure have thoroughly examined the intensity correction method conforming to the restricted least square method, as first described. As a result, the intensity correction method conforming to the restricted least square method has been understood as being considerably improved in accuracy compared to the intensity correction method conforming to the inverse matrix method disclosed in Japanese Unexamined Patent Application Publication No. 2003-83894. However, the proposers of the present disclosure have concluded that the following should be considered in the intensity correction method conforming to the restricted square method.

For example, in an operation of singly dyeing a sample to be measured with each pigment and measuring the fluorescence spectrum, time and effort of the measurement and a specimen used in the measurement may be unnecessarily wasted in many cases. Further, when cells are particularly focused on as a measurement target, it is difficult to prepare cells having the completely identical conditions by the number of pigments. In the restricted least square method, the base vector is common in all of the measurement data. However, in effect, it is natural to consider non-uniformity as being present in the base vector in each measurement due to various causes. Of course, the measurement data obtained by singly dyeing the multi-dyed cells may not be obtained. That is, originally, there is a base vector which may not be known. In consideration of these thoughts, the proposers of the present disclosure have noticed that the non-uniformity of the base vector itself should be considered and an error of the intensity correction process can be suppressed by considering the non-uniformity of the base vector.

The case in which the measurement data of a sample singly dyed with a given pigment is used as the base vector has been described. For example, the autofluorescence of cells or fluorescence originating from a tube or a chip of a micro-flow passage of a flow cytometer can be, of course, used as the base vector. In consideration of the trouble of preparing a single-dyed sample of cells or the like, as described above, beads (latex beads or the like) are singly dyed instead of the sample of cells or the like. However, the fluorescence spectrum may be used as the base vector. However, the average of the fluorescence spectra of the single-dyed beads may deviate from the fluorescence spectrum of the single-dyed sample of cells or the like. Therefore, when the base vector generated from the fluorescence spectrum of the beads is used, the result of the fluorescence intensity process may be considerably different from a case in which the base vector generated from the fluorescence spectrum of the sample of cells or the like is used. The proposers of the present disclosure have considered this point and have repeatedly examined a diversity of the measurement data available as the base vector.

In the restricted least square method described above, it is implicitly supposed that the fluorescence intensities in a plurality of frequency bands obtained from a plurality of optical detectors have non-uniform noise to the same degree. However, in the optical detector which is a representative example of a photomultiplier tube, there is a range in the signal intensity measurable with a proper S/N ratio. Therefore, when the restricted least square method is applied to the measurement data obtained without consideration of the sensitivity of each optical detector, there is a concern that the result of the intensity correction process is badly affected.

Accordingly, the proposers of the present disclosure have further made the examination based on the above-mentioned thought and have devised an intensity correction method of performing an intensity correction process with higher accuracy by eliminating error causes of the intensity correction process based on the non-uniformity of the base vector. Further, the proposers of the present disclosure have examined the diversity of the measurement data available as the base vector and the detection accuracy of the optical detector in addition to the improvement in the accuracy of the intensity correction process and have formulated an idea for the examination.

First Embodiment

Hereinafter, a first embodiment of the present disclosure will be described in detail with reference to FIGS. 5 to 9.
<Information Processing System>

Figure 5:
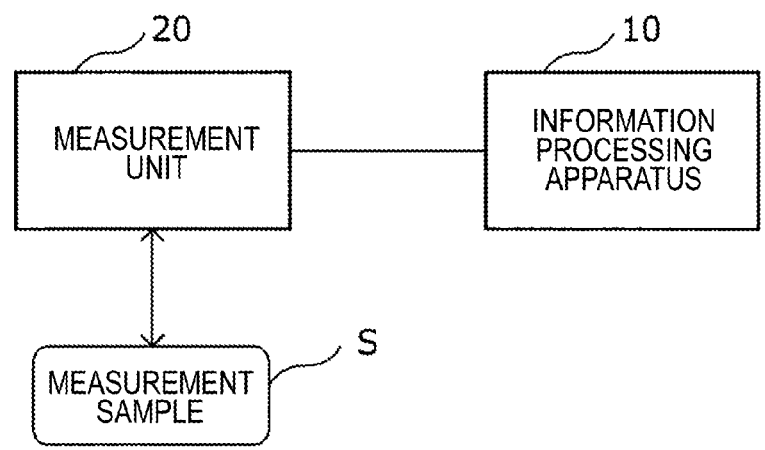
FIG. 5 is a diagram illustrating an information processing system according to a first embodiment of the present disclosure.

First, an information processing system according to this embodiment will be described with reference to FIG. 5. FIG. 5 is a diagram illustrating the information processing system according to this embodiment.

An information processing system 1 according to this embodiment includes an information processing apparatus 10 and various measurement units 20 that measure the spectrum of a measurement sample S, as shown in FIG. 5.

For example, biological microparticles such as cells, microbes, or liposomes or synthetic particles such as latex particles, gel particles, or industrial particles can be used as the microparticles which are the measurement sample S in this embodiment.

Examples of the biological microparticles include chromosome of various cells, liposomes, mitochondria, and organelles (cell organelles). Examples of the cells include animal cells (blood cells) and plant cells. Examples of microbes include bacilli such as colon bacilli, viruses such as tobacco mosaic viruses, and fungi such as yeast. Examples of the biological microparticles may include nucleic acids, proteins, and biological polymers such as composites thereof.

Examples of the industrial particles include organic polymeric materials, inorganic polymeric materials, and metals. Examples of the organic polymeric materials include polystyrene, styrene vinylbenzene, and polymethylmethacrylate. Examples of the inorganic polymeric materials include glass, silica, and magnetic materials. Examples of the metals include gold colloid and aluminum. In many cases, the microparticles are spherical, but may be not spherical. Further, the size, mass, and the like of the microparticles are not particularly limited.

The information processing apparatus 10 acquires the measurement data of the measurement sample S measured by the measurement units 20 and performs an intensity correction process of correcting the intensity of a spectrum which is the acquired measurement data. In FIG. 5, the information processing apparatus 10 according to this embodiment is provided as an apparatus different from the measurement units 20. However, a function of the information processing apparatus 10 according to this embodiment may be implemented by a computer that controls the measurement units 20 or may be implemented by an arbitrary computer installed in a casing of the measurement units 20. The detailed configuration of the information processing apparatus 10 will be described in detail below.

The measurement unit 20 irradiates a laser beam to the measurement sample S to measure emission of light such as the fluorescence or the phosphorescence from the measurement sample S, and measures the scattered light from the measurement sample S or measures the absorption spectrum from the measurement sample S. The measurement unit 20 according to this embodiment may measure the emission spectrum, the scatter spectrum, or the absorption spectrum of the measurement sample S or may measure at least two or more of the emission spectra, the scatter spectra, or the absorption spectra of the measurement sample S. These spectra are examples of "light intensity distributions" mentioned in the embodiment of the present disclosure.

Figure 6A:
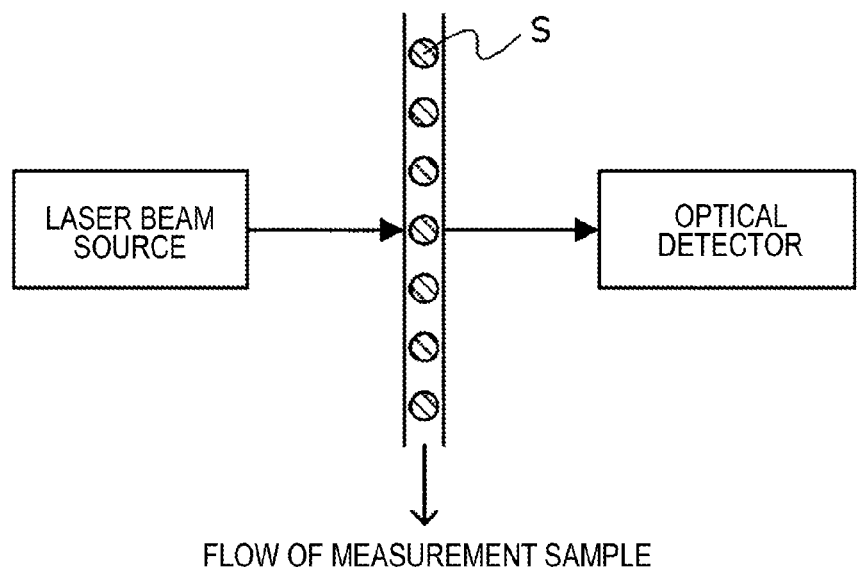
FIG. 6A is a diagram illustrating an example of a measurement unit according to the first embodiment.
Figure 6B:
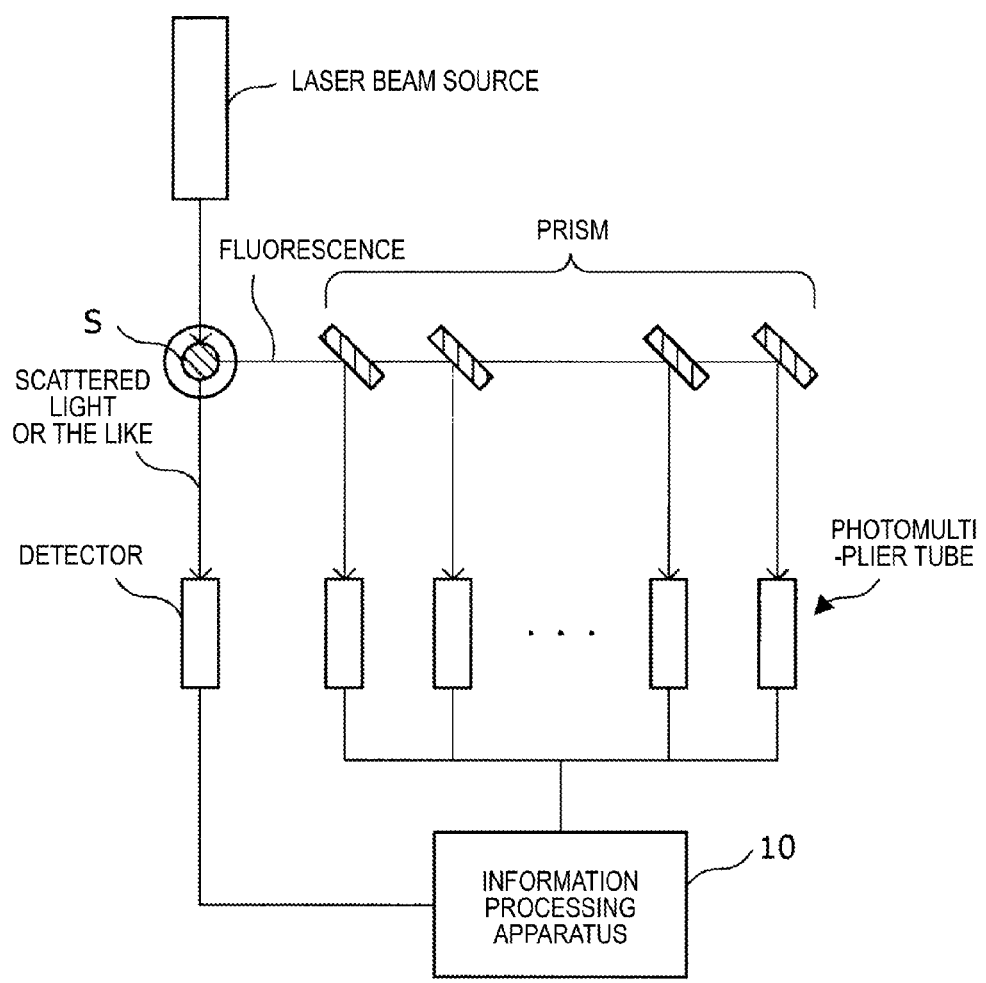
FIG. 6B is a diagram illustrating an example of the measurement unit according to the first embodiment.

Hereinafter, a case in which a flow cytometer measuring the fluorescence spectrum of the measurement sample S, as shown in FIGS. 6A and 6B, is used as the measurement unit 20 will be described in detail.

<Measurement Sample>

The microparticles are multi-marked (multi-dyed) as a measurement sample with a plurality of fluorescent pigments before the measurement of the fluorescence spectrum. The marking of the microparticles with the fluorescent pigments can be performed in accordance with any known method. For example, when cells are a measurement target, a fluorescence-marked antibody for cell-surface molecules is mixed with the cells and the antibody is bonded with the cell-surface molecules. The fluorescence-marked antibody may be a combination in which a fluorescent pigment is directly bonded with the antibody or may be a combination in which a fluorescent pigment having avidin bonded with a biotin-marked antibody is bonded by an avidin-biotin reaction. Further, the antibody may be a monoclonal antibody or a polyclonal antibody.

Two or more known substances can be combined in the fluorescent pigment used to multi-mark the microparticles. Examples of the fluorescent pigment include phycoerythrin (PE), FITC, PE-Cy5, PE-Cy7, PE-Texas red, allophycocyanin (APC), APC-Cy7, ethidium bromide, propidium iodide, Hoechst 33258/33342, DAPI, acridine orange, chromomycin, mithramycin, olivomycin, pyronin Y, thiazole orange, rhodamine 101, isothiocyanate, BCECF, BCECF-AM, C.SNARF-1, C.SNARF-1-AMA, aequorin, Indo-1, Indo-1-AM, Fluo-3, Fluo-3-AM, Fura-2, Fura-2-AM, oxonol, Texas red, rhodamine 123, 10-N-nonyl acridine orange (acridine orange), fluorescein, fluorescein diacetate, carboxyfluorescein, carboxyfluorescein diacetate, carboxydichlorofluorescein, and carboxydichlorofluorescein diacetate. Of course, the fluorescent pigment available in this embodiment is not limited to these examples.

<Example of Measurement Unit>

As shown in FIG. 6A, the flow cytometer which is an example of the measurement unit 20 emits a laser beam with a wavelength capable of exciting a fluorescent pigment used to dye the sample S, to the multi-dyed microparticles S flowing along a micro-flow passage from a laser light source. The optical detector such as a photomultiplier tube installed in the flow cytometer detects the fluorescence released from the microparticles radiated with the laser beam. Further, in the example of FIG. 6A, only one laser light source is illustrated, but a plurality of laser light sources may be provided.

The flow cytometer performing the measurement may have a known configuration, but a configuration in FIG. 6B is shown for example.

As shown in FIG. 6B, the flow cytometer includes a laser light source that emits a laser beam (for example, a laser beam with wavelengths of 488 nm or 640 nm) with a predetermined wavelength, an optical system (not shown), such as a lens, that guides the laser beam to the measurement sample S, various optical detectors that detect scattered light, such as forward-scattered light or backward-scattered light, or the fluorescence from the measurement sample S, and various optical systems that guide the scattered light or the fluorescence to the optical detectors.

Here, in the example of FIG. 6B, detectors such as charge coupled devices (CCD), complementary metal oxide semiconductors (CMOS), or photodiodes that detect the scattered light from the measurement sample S and a plurality of (for example, thirty-two) photomultiplier tubes that detect the fluorescence from the measurement sample S are installed as the optical detectors. Further, when the technology of this embodiment is applied, the number of optical detectors may be set to be greater than the number of fluorescent pigments used to multi-dye the measurement sample S. That is, when the intensity correction process described below in this embodiment is applied, a desired result can be obtained with high accuracy even under the set condition of "(number of fluorescent pigments)<(number of optical detectors)."

The fluorescence from the measurement sample S resulting from the laser beam emitted from a laser beam source is spectrally separated by a prism installed between the measurement sample S and each photomultiplier tube, and then is guided to each photomultiplier tube. Each photomultiplier tube outputs measurement data indicating the detection result of the fluorescence having the corresponding wavelength band to the information processing apparatus 10 according to this embodiment.

As described above, the information processing apparatus 10 according to this embodiment obtains fluorescence spectra obtained through the continuous measurement of the fluorescence from the measurement sample S. Further, the measurement data of the scattered light or the like detected by the detector such as a CCD, a CMOS, or a photodiode may be configured to be output to the information processing apparatus 10 according to this embodiment.

In the example of the flow cytometer shown in FIG. 6B, a series of optical systems is installed to detect the scattered light from the measurement sample S, but the optical systems may not be installed. In the flow cytometer shown in FIG. 6B, the fluorescence from the measurement sample S is spectrally separated by the prisms, and then is guided to the photomultiplier tubes. However, the fluorescence from the measurement sample S may be separated by a plurality of wavelength selection filters and may be guided to the photomultiplier tubes. That is, some of the constituent elements may be arbitrarily modified, as long as the fluorescence spectrum obtained by exciting the multi-dyed sample S by the laser beam can be selectively measured for each predetermined wavelength band and the measurement result can be input to the information processing apparatus 10.

An example of the measurement unit 20 according to this embodiment has been described simply with reference to FIGS. 6A and 6B.

<Information Processing Apparatus>

Figure 8:
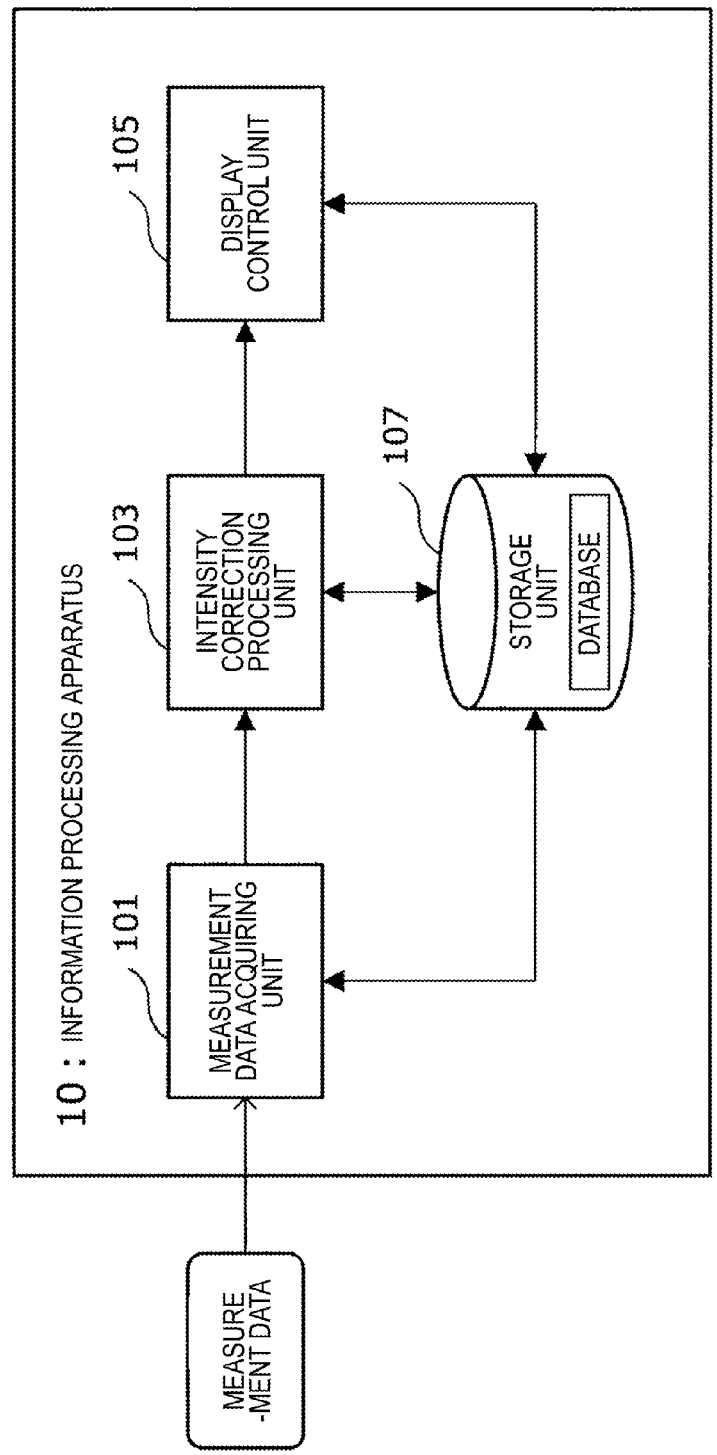
FIG. 8 is a block diagram illustrating an example of the configuration of the information processing apparatus according to the first embodiment.
Figure 9:
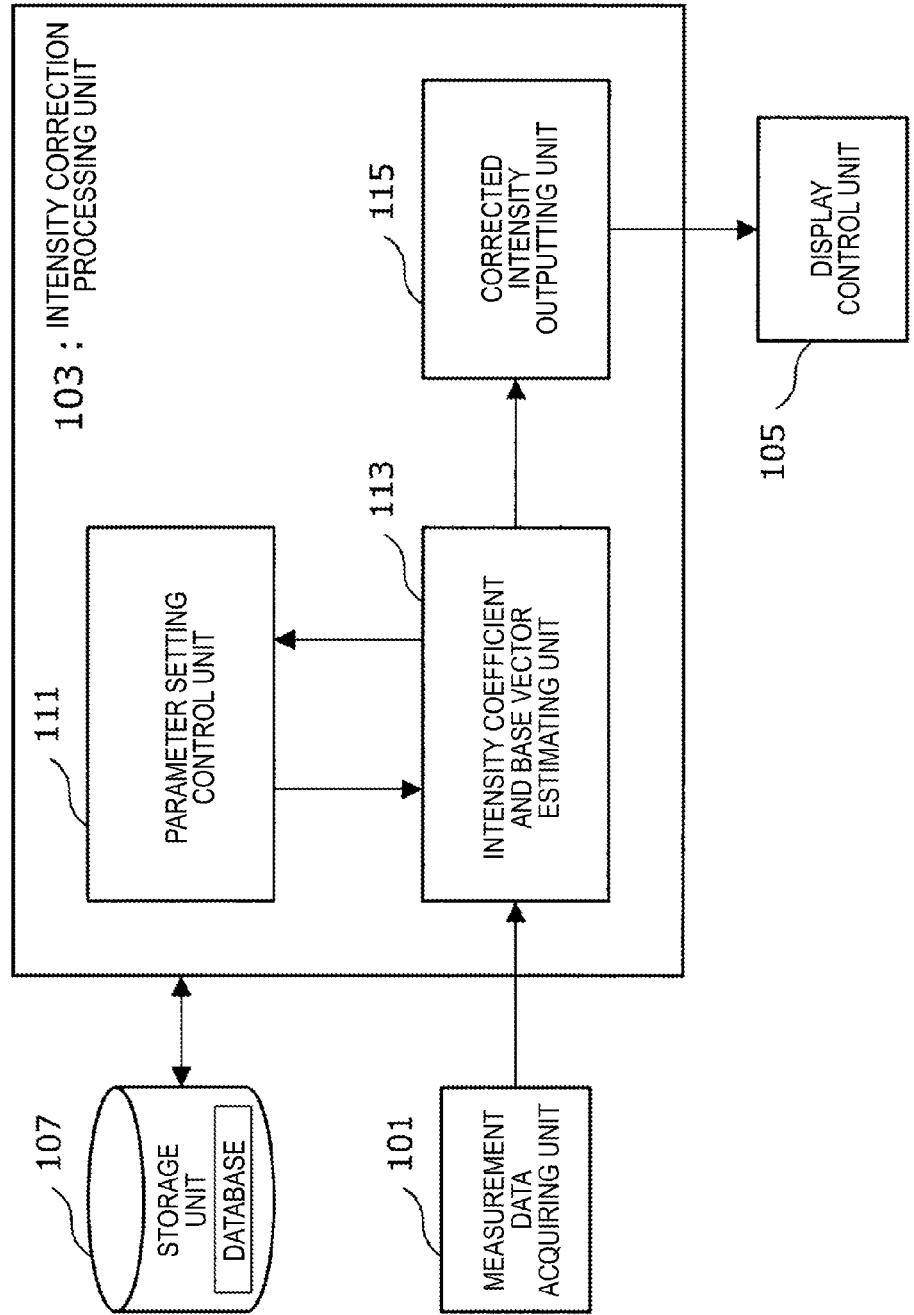
FIG. 9 is a block diagram illustrating an example of the configuration of an intensity correction processing unit according to the first embodiment.

Next, the information processing apparatus 10 according to this embodiment will be described in detail with reference to FIGS. 7 to 9. FIG. 7 is a diagram schematically illustrating the intensity correction process of the information processing apparatus 10 according to this embodiment. FIG. 8 is a block diagram illustrating the configuration of the information processing apparatus 10 according to this embodiment. FIG. 9 is a block diagram illustrating the configuration of an intensity correction processing unit 103 of the information processing apparatus 10 according to this embodiment.

[Overview of Information Processing Apparatus]

As shown in FIG. 7, the information processing apparatus 10 according to this embodiment deals with "the measurement data as a result obtained by superimposing noise on a linear sum of multiplications of the base vectors used in the intensity correction process and the intensity coefficients." Moreover, the information processing apparatus 10 models the base vectors using a predetermined distribution (for example, a truncated normal distribution) and also models the noise using a predetermined distribution (for example, a normal distribution). Then, the information processing apparatus 10 performs the intensity correction process based on a probability model. Hereinafter, the predetermined distribution indicating the base vectors is also referred to as a prior distribution.

The information processing apparatus 10 according to this embodiment improves non-uniformity of the base vectors in each measurement by modeling the base vectors using the predetermined distribution, estimating the base vector in each measurement data based on the probability model, and correcting the prior distribution. Thus, it is possible to estimate the base vector of each measurement data (each measurement spectrum) or estimate a base vector common to each measurement data.

The information processing apparatus 10 according this embodiment can estimate the base vector. Therefore, since not only the base vector of the fluorescent pigment but also the very fluorescence of a measurement sample of cells or the like or a micro-flow passage chip can be estimated, the measurement data available as the base vector can be diversified. Further, the information processing apparatus 10 according to this embodiment can also use a spectrum measured in advance or prior knowledge such as a database regarding the spectrum as an initial value of the prior distribution.

The information processing apparatus 10 according to this embodiment can realize the intensity correction process in consideration of the sensitivity of each optical detector by modeling a vector (noise vector) indicating noise using a normal distribution with variances which have no correlation and are different in each dimension, and estimating the variance of the noise of each dimension.

[Configuration of Information Processing Apparatus]

Next, the configuration of the information processing apparatus 10 according to this embodiment will be described in detail with reference to FIGS. 8 and 9.

Overall Configuration of Information Processing Apparatus

As exemplified in FIG. 8, the information processing apparatus 10 according to this embodiment includes a measurement data acquiring unit 101, an intensity correction processing unit 103, a display control unit 105, and a storage unit 107.

The measurement data acquiring unit 101 is realized by a central processing unit (CPU), a read-only memory (ROM), a random access memory (RAM), an input device, a communication device, and the like. The measurement data acquiring unit 101 acquires the measurement data of the measurement sample S generated by the measurement units 20 from the measurement units 20.

Here, for example, the measurement data of the measurement sample S acquired from the measurement unit 20 is data that indicates the intensity of a spectrum produced by irradiating a laser beam with a predetermined wavelength to one microparticle or a predetermined number of microparticles. In the measurement of the spectrum of one microparticle or the predetermined number of microparticles, there is a time duration although the time duration is minute. Therefore, in the measurement data according to this embodiment, an accumulated intensity, the maximum intensity, an average intensity, or the like of the minute time duration is used.

When the measurement data acquiring unit 101 acquires the measurement data of the interest measurement sample S, the measurement data acquiring unit 101 inputs the acquired measurement data to the intensity correction processing unit 103 to be described below. The measurement data acquiring unit 101 may store, as history information, the acquired measurement data in the storage unit 107 or the like described below in association with temporal information such as an acquisition date or the like of the measurement data.

The intensity correction processing unit 103 is realized by a CPU, a digital signal processor (DSP), a ROM, a RAM, and the like. The intensity correction processing unit 103 performs the intensity correction process on various spectra measured by the measurement units 20 based on the measurement data of the measurement sample S output from the measurement data acquiring unit 101 or a prior knowledge database of the base vectors stored in the storage unit 107 or the like to be described below. The intensity correction processing unit 103 according to this embodiment calculates a genuine intensity for each base vector in accordance with the intensity correction method simply described above. Therefore, the calculated genuine intensity is more accurate even compared to the result obtained by the intensity correction method using the restricted least square method.

The intensity correction processing unit 103 inputs the result of the intensity correction process performed on various spectra output from the measurement data acquiring unit 101 to the display control unit 105 to be described below and allows the display control unit 105 to present the processing result to a user. The intensity correction processing unit 103 may update various databases stored in the storage unit 107 or the like to be described below based on the obtained result of the intensity correction process.

The intensity correction processing unit 103 may allow an output apparatus such as a printer to output and present the obtained result of the intensity correction process as a printed material to the user or may output data indicating the obtained result of the intensity correction process to a USB memory or various recording media such as a CD, a DVD, or a Blu-ray disc. Further, the intensity correction processing unit 103 may output the data indicating the obtained result of the intensity correction process to an external apparatus, with which the information processing apparatus 10 according to this embodiment can communicate, via various communication networks.

The intensity correction processing unit 103 may store, as history information, the data indicating the obtained result of the intensity correction process in the storage unit 107 to be described below in association with temporal information such as a generation date of the data.

The configuration of the intensity correction processing unit 103 will be described in detail below.

The display control unit 105 is realized by a CPU, a ROM, a RAM, a communication device, an output device, and the like. The display control unit 105 controls the display of a display screen of a display apparatus such as a display included in the information processing apparatus 10 or a display apparatus such as a display installed outside the information processing apparatus 10. More specifically, the display control unit 105 controls the display of the display screen based on information regarding the results (corrected spectrum intensities) of the intensity correction process of the various spectra provided from the intensity correction processing unit 103. When the display control unit 105 controls the display of the display screen for the result of the intensity correction process provided from the intensity correction processing unit 103, the user of the information processing apparatus 10 can comprehend the result of the intensity correction process.

The storage unit 107 is realized by, for example, a RAM or a storage device included in the information processing apparatus 10 according to this embodiment. The storage unit 107 stores various databases used in the intensity correction process by the intensity correction processing unit 103, the information regarding the prior knowledge, or the like. The storage unit 107 may store various kinds of measurement data acquired by the measurement data acquiring unit 101. The storage unit 107 may also store execution data corresponding to various applications used for the intensity correction processing unit 103 or the display control unit 105 to display various kinds of information on the display screen. The storage unit 107 appropriately stores various parameters necessarily stored in a given process of the information processing apparatus 10, the progress of a process, various databases, and the like. The storage unit 107 is configured such that each processing unit of the information processing apparatus 10 according to this embodiment can freely read and write information.

Configuration of Intensity Correction Processing Unit

Next, the configuration of the intensity correction processing unit 103 of the information processing apparatus 10 according to this embodiment will be described in detail with reference to FIG. 9.

As described above, the intensity correction processing unit 103 according to this embodiment formulates the measurement data, as shown in FIG. 7, provides the prior distribution of the base vectors and the noise vectors, and estimates the base vector and the noise vector of each measurement data. Thereafter, the intensity correction processing unit 103 calculates the intensity coefficients in an expression shown in FIG. 7 using the estimated base vectors and the estimated noise vectors.

The intensity correction processing unit 103 calculates a posterior distribution of the base vector or the noise vector in each measurement data based on the initial value of the above-described prior distribution and updates a parameter indicating the prior distribution using the obtained posterior distribution. Thus, the prior distribution of the base vectors or the noise vectors used in the intensity correction process is frequently corrected so as to be suitable for the measurement data.

Here, the intensity correction processing unit 103 may store data regarding a typical prior distribution of an interest spectrum as a database in advance in the storage unit 107 or the like and may use the data regarding the typical prior distribution as the initial value of the prior distribution.

For example, when the fluorescence spectrum of cells dyed with various fluorescent pigments is focused on, the fluorescence spectrum can be measured using a single-dyed sample of cells or beads dyed with some or all of the fluorescent pigments, and the obtained fluorescence spectrum can be used as the initial value of the prior distribution. Further, the fluorescence spectrum measured using a mixture with a simply dyed sample of cells or beads or the fluorescence spectrum measured using a multi-dyed sample of cells or beads can also be used as the initial value of the prior distribution. The intensity correction processing unit 103 may update this initial value of the prior distribution using the posterior distribution of the estimated base vectors and may correct the measurement data to obtain proper measurement data.

To obtain the prior distribution of the base vectors using the mixture with the single-dyed sample, it is desirable to select the fluorescent pigments combined so that observation peaks of the spectral spectra of the corresponding fluorescent pigments slightly overlap.

The intensity correction processing unit 103 can define a prior distribution of a fluorescence spectrum of a chip or an autofluorescence spectrum of cells in addition to the base vector of the fluorescent pigment used to measure the fluorescence spectrum and gradually update the prior distribution. Thus, the intensity correction processing unit 103 can obtain the prior distribution of the fluorescence spectrum of a chip or an autofluorescence spectrum of cells through a learning process.

For example, the intensity correction processing unit 103 gradually corrects the defined prior distribution so as to be suitable based on the measurement data using the fluorescence spectrum measured without flow to a chip or the fluorescence spectrum measured by flow of only a liquid used to flow cells. Thus, the intensity correction processing unit 103 can obtain the prior distribution indicating the fluorescence spectrum of a chip. Likewise, the intensity correction processing unit 103 gradually corrects the defined prior distribution so as to be more suitable for the measurement data obtained through the measurement using a fluorescence spectrum measured by flowing undyed cells to a chip. The intensity correction processing unit 103 performs such processes to obtain the prior distribution indicating the autofluorescence spectrum of cells.

Here, the intensity correction processing unit 103 may not estimate the base vector in each measurement data, but may likewise estimate a base vector commonly available for all of the measurement data and calculate the intensity coefficient using the commonly available base vector. That is, the intensity correction processing unit 103 may estimate the base vector commonly available for all of the measurement data and use various parameters indicating the obtained base vector for each intensity correction process to calculate the intensity coefficient.

The configuration of the intensity correction processing unit 103 having such functions will be described in detail with reference to FIG. 9.

Hereinafter, the intensity correction processing unit 103 will be described in detail using mathematical expressions. At this time, measurement data (hereinafter, also referred to as a measurement vector) of a given event n (where $1 \leq n \leq N$) is expressed as $y_n \in R^K$ (where K is the number of channels of an optical detector). Further, a base vector of a half positive value corresponding to a factor i (where $1 \leq i \leq M$) is expressed as $\phi_{ni}$ (where $\phi_{ni} \geq 0$) and a coefficient (intensity coefficient) of the half positive value of the factor i is expressed as $w_{ni}$ (where $w_{ni} \geq 0$). Further, a matrix in which the base vectors are arranged is expressed as $\Phi_n = (\phi_{n1}, \ldots, \phi_{nM})$ and a vector in which the intensity coefficients are arranged is expressed as $w_n = w_{nm})^T$.

As exemplified in FIG. 9, the intensity correction processing unit 103 according to this embodiment includes a parameter setting control unit 111, an intensity coefficient and base vector estimating unit 113, and a corrected intensity outputting unit 115.

The parameter setting control unit 111 is realized by a CPU, a DSP, a ROM, a RAM, and the like. The parameter setting control unit 111 sets various parameters to be used in the intensity correction process, such as a parameter indicating a prior distribution of the base vectors and a parameter indicating a distribution of the noise vectors, and updates the values of these parameters in accordance with the processing result of the intensity coefficient and base vector estimating unit 113 to be described below.

Specifically, the parameter setting control unit 111 sets a prior distribution of the base vector $\phi_{ni}$ in an event n, as in Equation 101 below and also sets the distribution of the noise vector $\epsilon_n$, as in Equation 102.

$$\phi_{ni} \sim N_{\phi_{ni} \geq 0}(\mu_i, \Sigma_i) \quad \text{(Equation 101)}$$

$$\epsilon_n \sim N(0, \text{diag}(\lambda)^{-1}) \quad \text{(Equation 102)}$$

Here, Equation 101 above has a probability density proportional to a normal distribution with an average parameter and a covariance parameter $\Sigma_i$ in a range satisfying the base vector "$\phi_{ni} \geq 0$" and indicates a truncated normal distribution having no probability density in other ranges. In Equation 102 above, $\lambda = (\lambda_1, \ldots, \lambda_K)^T$ indicates the variance of each optical detector. Equation 102 above indicates an independent variance parameter $\lambda_k$ in each optical detector. Thus, by considering the variance, the intensity correction process in which the sensitivities of the optical detectors are considered can be realized, for example, when the sensitivities of the optical detectors are different from each other.

The parameter setting control unit 111 produces a probability model of a measurement vector $y_n$ corresponding to the measurement data, as in Equation 103 below, by setting the base vector and the noise vector, as in Equation 101 and Equation 102 above.

$$y_n \sim N_{y_n \geq 0}(\Phi_n w_n, \text{diag}(\lambda)^{-1}) \quad \text{(Equation 103)}$$

The parameter setting control unit 111 may not set the prior distribution of the base vector $\phi_n$, based on Equation 101, but may use various spectrum data stored in various databases or various spectra themselves measured in advance as the prior distribution of the base vectors $\phi_{ni}$, as described above.

The parameter setting control unit 111 updates the parameters and the noise vectors of the prior distributions using the $w_n$ or $\Phi_n$ calculated by the intensity coefficient and base vector estimating unit 113 to be described below. Specifically, the parameter setting control unit 111 updates the noise vectors based on Equation 104 below $$\lambda_k^{-1} = \frac{1}{N} \sum_{n=1}^{N} (y_{nk} - \varphi_{nk}^T w_n)^2 \quad \text{(Equation 104)}$$

k-th element of $\phi_{nk}^T : \Phi_n$

The parameter setting control unit 111 updates the average parameter $\mu_i$ and the covariance parameter $\Sigma_i$, which are the parameters of the prior distribution in accordance with a method such as type $\mu_i$ maximum likelihood estimation. A method of updating the average parameter $\mu_i$ and the covariance parameter $\Sigma_i$ can appropriately be set. For example, the parameter setting control unit 111 can update the average parameter $\mu_i$ and the covariance parameter $\Sigma_i$ so that an expected value E for $\{\phi_{ni}\}_{n=1}^{N}$ expressed by Equation 105 below is the maximum.

When the parameters are updated based on Equation 105 below, all of the base vectors $\phi_{ni}$ are equally reflected on the parameters $\mu_i$ and $\Sigma_i$. However, a case of the intensity coefficient "$w_{ni}=0$" is considered to be able to occur many times since the intensity coefficient vector $w_n$ is subjected to the estimation process under the restriction of "$w_n \geq 0$," as will be described below. In this case, the average of the base vectors $\phi_{ni}$ is $\mu_i$. Further, even when the value of the intensity coefficient $w_{ni}$ is small, the average of the base vectors $\phi_{ni}$ is likewise Accordingly, when the base vectors $\phi_{ni}$ are used in the updating process uniformly, there is a probability that the prior distribution may be dependent strongly on the initial value. Accordingly, the parameter setting control unit 111 may update the average parameter $\mu_i$ and the covariance parameter $\Sigma_i$ so that a weighted estimated value E is the maximum with the intensity coefficient $w_{ni}$, as in Equation 106 below. In addition to such a method, the parameter setting control unit 111 may perform an updating process using only the intensity coefficient equal to or greater than a threshold value obtained by multiplying the maximum value of $\{w_{ni}\}_{n=1}^{N}$ by a predetermined value.

$$E\left[\sum_{n=1}^{N} \ln p(\phi_{ni} | \mu_i, \Sigma_i)\right] \quad \text{(Equation 105)}$$

$$E\left[\sum_{n=1}^{N} w_{ni} \ln p(\phi_{ni} | \mu_i, \Sigma_i)\right] \quad \text{(Equation 106)}$$

The intensity coefficient and base vector estimating unit 113, which is an example of an estimation unit, is realized by a CPU, a DSP, a ROM, a RAM, and the like. The intensity coefficient and base vector estimating unit 113 estimates a likely intensity coefficient corresponding to the measurement vector $y_r$, and the base vector based on the measurement vector $y_n$ corresponding to the measurement data and the parameters (the parameters for the base vector and the noise vector) set by the parameter setting control unit 111.

When the intensity coefficient and base vector estimating unit 113 obtains estimated values of the intensity coefficient and the parameter of the base vector, the intensity coefficient and base vector estimating unit 113 performs convergence determination of determining whether the obtained estimated values converge. When the intensity coefficient and base vector estimating unit 113 determines that the obtained estimated values do not converge, the intensity coefficient and base vector estimating unit 113 outputs the obtained estimated values to the parameter setting control unit 111 and asks to update various parameters. Further, the intensity coefficient and base vector estimating unit 113 again estimates the intensity coefficient and the base vector using the updated various parameters.

The intensity coefficient and base vector estimating unit 113 according to this embodiment can estimate the likely intensity coefficient corresponding to the measurement vector and the base vector with high accuracy by repeatedly performing the above-described calculation.

When the intensity coefficient and base vector estimating unit 113 determines that the obtained estimated values converge, the intensity coefficient and base vector estimating unit 113 outputs the estimated value of the obtained intensity coefficient to the corrected intensity outputting unit 115 described below.

As the method used to estimate the intensity coefficient or the base vector, the intensity coefficient and base vector estimating unit 113 can use a known method such as maximum a posteriori (MAP) estimation, various Bayesian estimations such as Bayesian estimation or variational Bayesian estimation based on sampling, or maximum likelihood estimation. Further, during the process, the base vector estimated in accordance with MAP estimation or the like may be used without change. However, the base vector subjected to pre- $$p(\{y_n, w_n, \Phi_n\}_{n=1}^N, \lambda \mid \{\mu_i, \Sigma_i\}_{i=1}^M) = \qquad \text{(Equation 111)}$$

$$\prod_{n=1}^N \left( p(y_n \mid \Phi_n, w_n, \lambda) \prod_{i=1}^M p(\phi_{ni} \mid \mu_i, \Sigma_i) \right)$$

Here, when the logarithm of Equation 111 above is taken and the term of the intensity coefficient vector $w_n$ is focused on, Equation 112 below can be obtained. Since $w_n \geq 0$, the intensity coefficient and base vector estimating unit 113 solves a quadratic programming problem expressed by Equation 113 below under the condition of "$w_n \geq 0$" to obtain an optimum intensity coefficient vector $w_n$ that satisfies Equation 111 above and Equation 112.

$$\ln p(\{y_n, w_n, \Phi_n\}_{n=1}^N, \lambda \mid \{\mu_i, \Sigma_i\}_{i=1}^M) = -\frac{1}{2} \qquad \text{(Equation 112)}$$
$$\{w_n^T(\Phi_n^T \mathrm{diag}(\lambda)\Phi_n)w_n - 2y_n^T \mathrm{diag}(\lambda)\Phi_n w_n\} + const.$$

$$\hat{w}_n = \mathrm{argmin} w_n^T(\Phi_n^T \mathrm{diag}(\lambda)\Phi_n)w_n - 2y_n^T \mathrm{diag}(\lambda)\Phi_n w_n \qquad \text{(Equation 113)}$$

Further, when the logarithm of Equation 111 above is taken and the term of a base vector matrix $\Phi_n$ is focused on, Equation 114 below can be obtained. Here, in Equation 114 below, $\mathrm{diag}(\lambda)$ is a diagonal matrix that has $\lambda$ in a diagonal component, $\mathrm{diag}(\Sigma_1^{-1}, \ldots, \Sigma_M^{-1})$ is a block diagonal matrix that has "$\Sigma_1^{-1}, \ldots, \Sigma_M^{-1}$" in a diagonal block, and $I_K$ is a K-dimensional unit matrix. Further, in Equation 114 below, $\mathrm{vec}(c_n)$ is a vector expressed by Equation 115 below and $\mu$ is a vector expressed by Equation 116 below.

$$\ln p(\{y_n, w_n, \Phi_n\}_{n=1}^N, \lambda \mid \{\mu_i, \Sigma_i\}_{i=1}^M) = \qquad \text{(Equation 114)}$$

$$-\frac{1}{2}\left\{ \begin{array}{l} (y_n - (w_n^T \otimes I_K)\mathrm{vec}(\Phi_n))^T \mathrm{diag}(\lambda)(y_n - (w_n^T \otimes I_K)\mathrm{vec}(\Phi_n)) + \\ (\mathrm{vec}(\Phi_n) - \mu)^T \mathrm{diag}(\Sigma_1^{-1}, \ldots, \Sigma_M^{-1})(\mathrm{vec}(\Phi_n) - \mu) \end{array} \right\} =$$

$$-\frac{1}{2}\left[ \begin{array}{l} \mathrm{vec}(\Phi_n)^T\{(w_n^T \otimes I_K)^T \mathrm{diag}(\lambda)(w_n^T \otimes I_K) + \mathrm{diag}(\Sigma_1^{-1}, \ldots, \Sigma_M^{-1})\}\mathrm{vec}(\Phi_n) - \\ 2\{(w_n^T \otimes I_K)^T \mathrm{diag}(\lambda)y_n + diag(\Sigma_1^{-1}, \ldots, \Sigma_M^{-1})\mu\}^T \mathrm{vec}(\Phi_n) \end{array} \right]$$

($\otimes$: Kronecker product)

$$\mathrm{vec}(\Phi_n) = \begin{pmatrix} \phi_{n1} \\ \vdots \\ \mu_{nM} \end{pmatrix} \qquad \text{(Equation 115)}$$

$$\mu = \begin{pmatrix} \mu_1 \\ \vdots \\ \mu_M \end{pmatrix} \qquad \text{(Equation 116)}$$

determined normalization can be considered for use. For example, a normalization method using the maximum value or a value of an integral of the fluorescence spectrum and a normalization method using a norm (for example, the Euclidean norm) of the base vector can be considered as the normalization method.

Hereinafter, a case in which the intensity coefficient and base vector estimating unit 113 performs the estimation process using the MAP estimation will be described in detail.

First, the intensity coefficient and base vector estimating unit 113 performs the MPS estimation on $\{w_n, \Phi_n\}_{n=1}^N$ and $\lambda$ set by the parameter setting control unit 111. At this time, a simultaneous distribution considered by the intensity coefficient and base vector estimating unit 113 is expressed as in Equation 111 below.

Here, since $\Phi_n \geq 0$, the intensity coefficient and base vector estimating unit 113 solves a quadratic programming problem expressed by Equation 117 below under the restriction of "$\Phi_n \geq 0$" to obtain an optimum intensity coefficient vector $\Phi_n$ that satisfies Equation 111 and Equation 114 above.

$$\mathrm{vec}(\Phi_x) = \arg\min \mathrm{vec}(\Phi_x)^T\{(w_x^T \otimes I_K)^T \mathrm{diag}(\lambda)(w_x^T$$
$$\otimes I_K) + \mathrm{diag}(\Sigma_1^{-1}, \ldots, \Sigma_M^{-1})\}\mathrm{vec}(\Phi_x) - 2\{(w_x^T$$
$$\otimes I_K)^T \mathrm{diag}(\lambda)y_n + \mathrm{diag}(\Sigma_1^{-1}, \ldots, \Sigma_M^{-1})\mu\}^T \mathrm{vec}$$
$$(\Phi_x) \qquad \text{(Equation 117)}$$

The corrected intensity outputting unit 115 which is an example of an output unit is realized by a CPU, a ROM, a RAM, a communication device, and the like. The corrected intensity outputting unit 115 outputs the converged intensity coefficient $w_{ni}$ provided from the intensity coefficient and base vector estimating unit 113 as an intensity (corrected intensity) obtained through the intensity correction process on the interest measurement data.

For example, the corrected intensity outputting unit 115 inputs the intensity coefficient $w_{ni}$ provided from the intensity coefficient and base vector estimating unit 113 to the display control unit 105 and allows the display control unit 105 to output the corrected intensity to the user on the display screen. The corrected intensity outputting unit 115 may output the corrected intensity to the user via an output apparatus such as a printer or may output data indicating the corrected intensity to a USB memory or various recording media such a CD, a DVD, or a Blu-ray disc. The corrected intensity outputting unit 115 may output the data indicating the obtained corrected intensity to an external apparatus, with which the information processing apparatus 10 according to this embodiment can communicate, via various communication networks.

The configuration of the intensity correction processing unit 103 according to this embodiment has been described above in detail with reference to FIG. 9.

The case in which the prior distribution of the base vectors or the noise vectors is a normal distribution has been described above. However, the prior distribution may be a distribution other than the normal distribution, such as a Student-t distribution, a Laplace distribution.

When the intensity correction process is performed on the fluorescence spectrum of cells, the autofluorescence of the cells is considered to be different for each kind of cells. Therefore, the prior distribution of the base vectors corresponding to the autofluorescence of the cells may be a mixture distribution. Therefore, an estimation process of estimating the autofluorescence of the cells while estimating the kind of cells can be performed.

Here, the mixture distribution used in the prior distribution of the base vectors corresponding to the autofluorescence of the cells can be generated by processing a measurement vector group measured using an undyed cell group by an expectation maximization (EM) algorithm, a variational Bayesian estimation algorithm, or clustering.

The intensity correction process according to this embodiment performed, for example, on the fluorescence spectrum of the multi-dyed cells has been described above. However, the intensity correction process according to this embodiment is applicable to a spectrum other than the fluorescence spectrum of the multi-dyed cells.

For example, the intensity correction method according to this embodiment is also applicable to a case in which, when a mixture in which a plurality of compounds are considered to be mixed is focused on, the fluorescence spectrum, an absorption spectrum, a scattering spectrum, or the like of the mixture is subjected to the intensity correction using known spectrum databases of the respective compounds. In this case, the corrected intensity obtained in accordance with the intensity correction method according to this embodiment corresponds to a quantitative analysis result that shows how much a corresponding compound is contained. In the intensity correction method according to this embodiment, the base vector is estimated using a known spectrum database or the like based on an actually measured spectrum. Therefore, it is possible to obtain not only the quantitative analysis but also knowledge concerning which compound is mixed (that is, a qualitative analysis of the mixed compound).

The examples of the functions of the information processing apparatus 10 according to this embodiment have been described above. The constituent elements may be configured using general members or circuits or may be configured by hardware specialized for the functions of the constituent elements. Further, all of the functions of the constituent elements may be executed by a CPU or the like. Accordingly, the configuration to be used can be modified appropriately in accordance with a technical level when this embodiment is realized.

A computer program configured to realize the above-described functions of the information processing apparatus according to the embodiment may be developed and mounted on a personal computer or the like. Further, a computer-readable recording medium storing the computer program can be provided. Examples of the recording medium include a magnetic disk, an optical disc, a magneto-optical disc, and a flash memory. Further, the computer program may be delivered via, for example, a network without using the recording medium.

<Flow of Information Processing Method>

Figure 10:
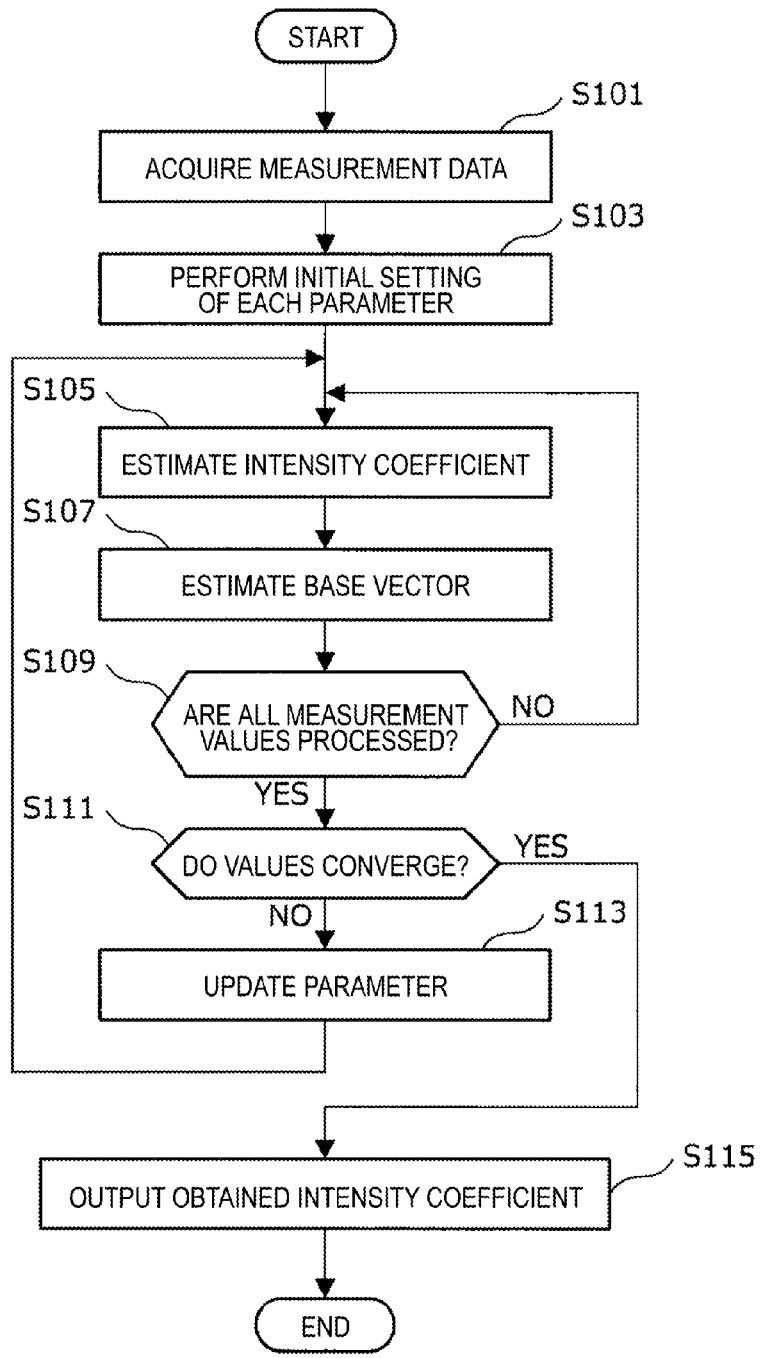
FIG. 10 is a flowchart illustrating an example of the flow of an information processing method according to the first embodiment.

Next, an example of the flow of an information processing method (intensity correction method) according to this embodiment will be described simply with reference to FIG. 10. FIG. 10 is a flowchart illustrating an example of the flow of the information processing method according to this embodiment.

The measurement data acquiring unit 101 of the information processing apparatus 10 according to this embodiment acquires data (measurement data) of the spectrum measured by the measurement unit 20 (step S101) and outputs the acquired measurement data to the intensity correction processing unit 103.

The parameter setting control unit 111 of the intensity correction processing unit 103 performs initial setting of the parameters of the base vectors and the noise vectors (step S103) and outputs information regarding the set parameters to the intensity coefficient and base vector estimating unit 113.

The intensity coefficient and base vector estimating unit 113 estimates the intensity coefficient using, for example, Equation 113 above based on the measurement data provided from the measurement data acquiring unit 101 and the various parameters set by the parameter setting control unit 111 (step S105). Then, the intensity coefficient and base vector estimating unit 113 estimates the base vector using, for example, Equation 117 above based on the measurement data provided from the measurement data acquiring unit 101 and the various parameters set by the parameter setting control unit 111 (step S107).

Here, the intensity coefficient and base vector estimating unit 113 determines whether all of the measurement values are processed (step S109). When not all of the measurement values are processed, the intensity coefficient and base vector estimating unit 113 returns the process to step S105 to continue the process. Conversely, when all of the measurement values are processed, the intensity coefficient and base vector estimating unit 113 determines that the obtained estimated values converge (step S111).

When the estimated values do not converge, the intensity coefficient and base vector estimating unit 113 outputs the obtained estimated values to the parameter setting control unit 111. The parameter setting control unit 111 updates the parameters of the base vectors and the noise vectors based on the provided estimated values (step S113) and outputs the updated parameters to the intensity coefficient and base vector estimating unit 113. The intensity coefficient and base vector estimating unit 113 returns the process to step S105 to continue the process using the updated parameters.

Conversely, when the estimated values converge, the intensity coefficient and base vector estimating unit 113 outputs the obtained intensity coefficient to the corrected intensity outputting unit 115. The corrected intensity outputting unit 115 outputs the intensity coefficient output from the intensity coefficient and base vector estimating unit 113 as the intensity (that is, the genuine intensity) subjected to the correction process (step S115). Thus, the user can understand the result of the intensity correction process on the interest spectrum.

An example of the flow of the information processing method according to this embodiment has been described simply with reference to FIG. 10.

<Example of Flow of Fluorescence Intensity Correction Method>

Next, an example of the flow of a process of correcting the fluorescence intensity of the fluorescence spectrum of the multi-dyed cells will be described with reference to FIGS. 11 to 16.

[Flow of General Fluorescence Intensity Correction Process]

Figure 11:
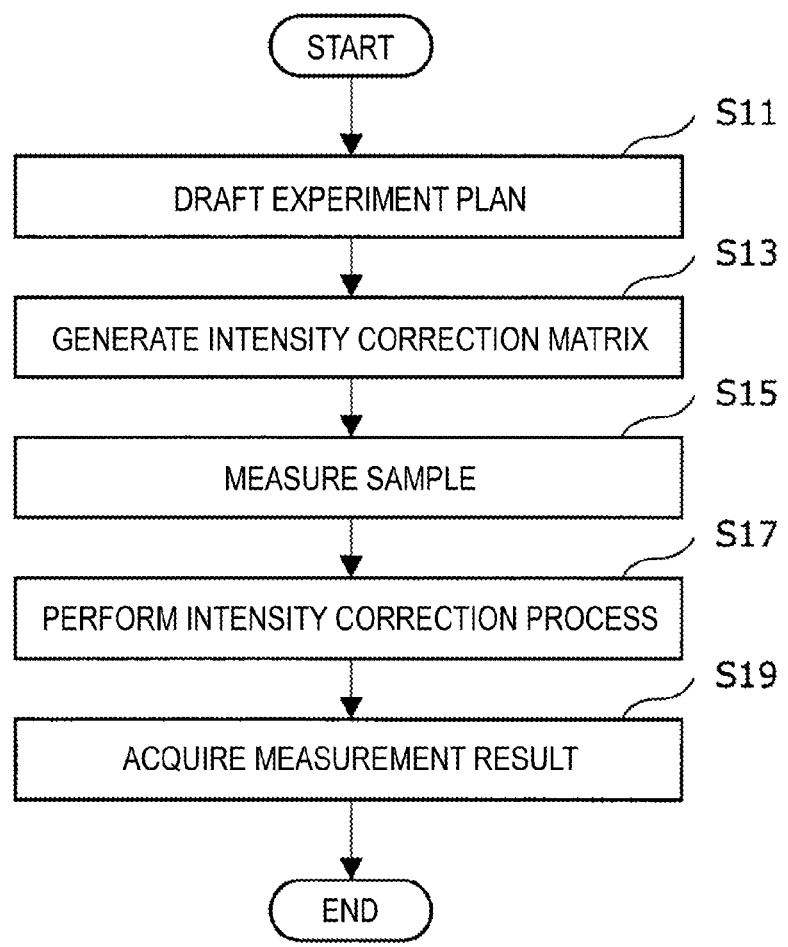
FIG. 11 is a flowchart illustrating the flow of a fluorescence intensity correction process.
Figure 12:
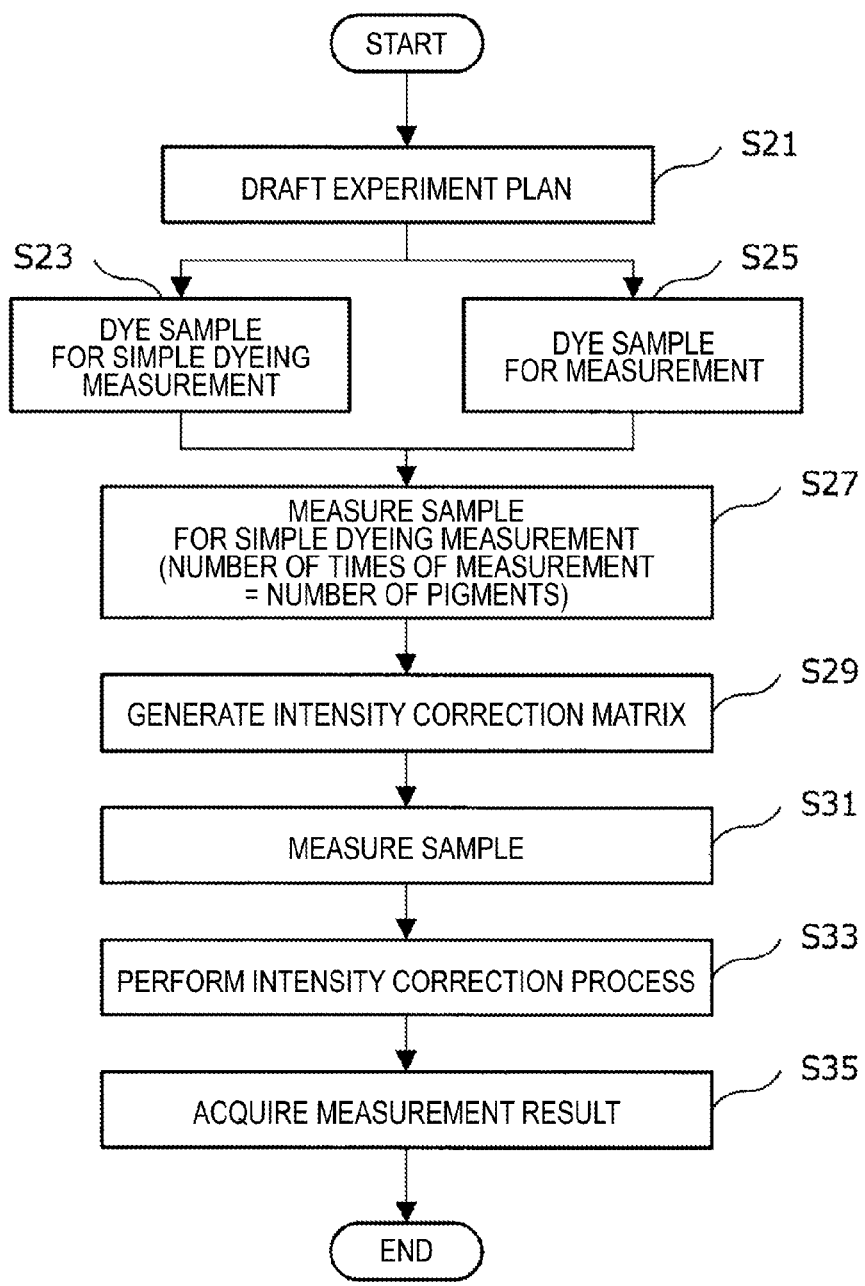
FIG. 12 is a flowchart illustrating the flow of the fluorescence intensity correction process.

The flow of a fluorescence intensity correction method will be described simply with reference to FIGS. 11 and 12 when the intensity correction method according to this embodiment is not used. FIGS. 11 and 12 are flowcharts illustrating the flow of the general fluorescence intensity correction process.

First, the flow of the fluorescence intensity correction process will be described with reference to FIG. 11, when the fluorescence spectrum of the single-dyed sample is not measured.

When the intensity correction method according to this embodiment is not used, a measurer of the fluorescence spectrum drafts an experiment plan to perform multi-dyeing on cells to be measured with given fluorescent pigments (step S11). Then, the measurer of the fluorescence spectrum generates an intensity correction matrix (compensation matrix), as in Equation 11, using a calculation apparatus such as a computer with reference to a database of the fluorescence characteristics of the fluorescent pigments (step S13).

Thereafter, the measurer of the fluorescence spectrum measures the fluorescence spectrum of the interest multi-dyed cells using a known flow cytometer or the like (step S15). Then, the measurer of the fluorescence spectrum performs the intensity correction process based on the generated intensity correction matrix using the calculation apparatus such as a computer (step S17) and acquires the measurement result (step S19).

Next, the flow of the measurement of the fluorescence spectrum of the single-dyed sample will be described with reference to FIG. 12.

When the intensity correction method according to this embodiment is not used, the measurer of the fluorescence spectrum drafts an experiment plan to perform multi-dyeing of cells to be measured with given fluorescent pigments (step S21). Then, the measurer of the fluorescence spectrum dyes a sample for simple dyeing measurement (step S23) and also dyes a sample to be measured (step S25).

Thereafter, the measurer of the fluorescence spectrum measures the fluorescence spectrum of the sample using the single dyeing measurement prepared in step S23 (step S27). At this time, when the intensity correction method according to this embodiment is not used, the number of times the sample for single dyeing measurement is measured is same as the number of fluorescent pigments used to multi-dye the cells. When the measurement of the sample for the simple dyeing measurement ends, the measurer of the fluorescence spectrum generates the same intensity correction matrix as Equation 11 using the calculation apparatus such as a computer (step S29).

After performing the pre-processing described above, the measurer of the fluorescence spectrum measures the fluorescence spectrum of the interest multi-dyed cells using a known flow cytometer or the like (step S31). Then, the measurer of the fluorescence spectrum performs the intensity correction process based on the generated intensity correction matrix using the calculation apparatus such as a computer (step S33) and acquires the measurement result (step S35).

[Flow of Fluorescence Intensity Correction Process Using Intensity Correction Method According to Embodiment]

Figure 13:
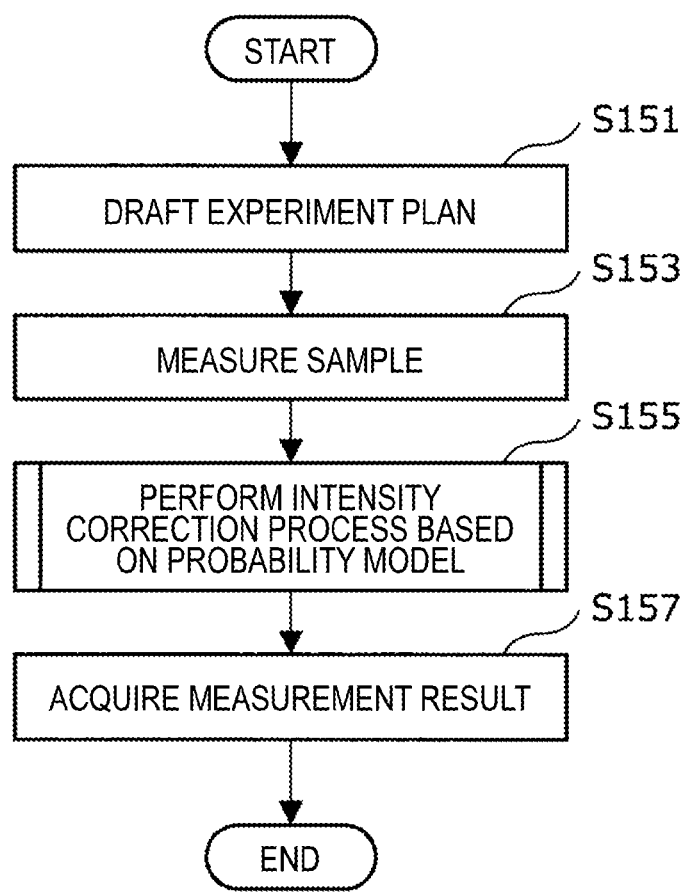
FIG. 13 is a flowchart illustrating an example of the flow of the fluorescence intensity correction process using the information processing method according to the first embodiment.
Figure 14:
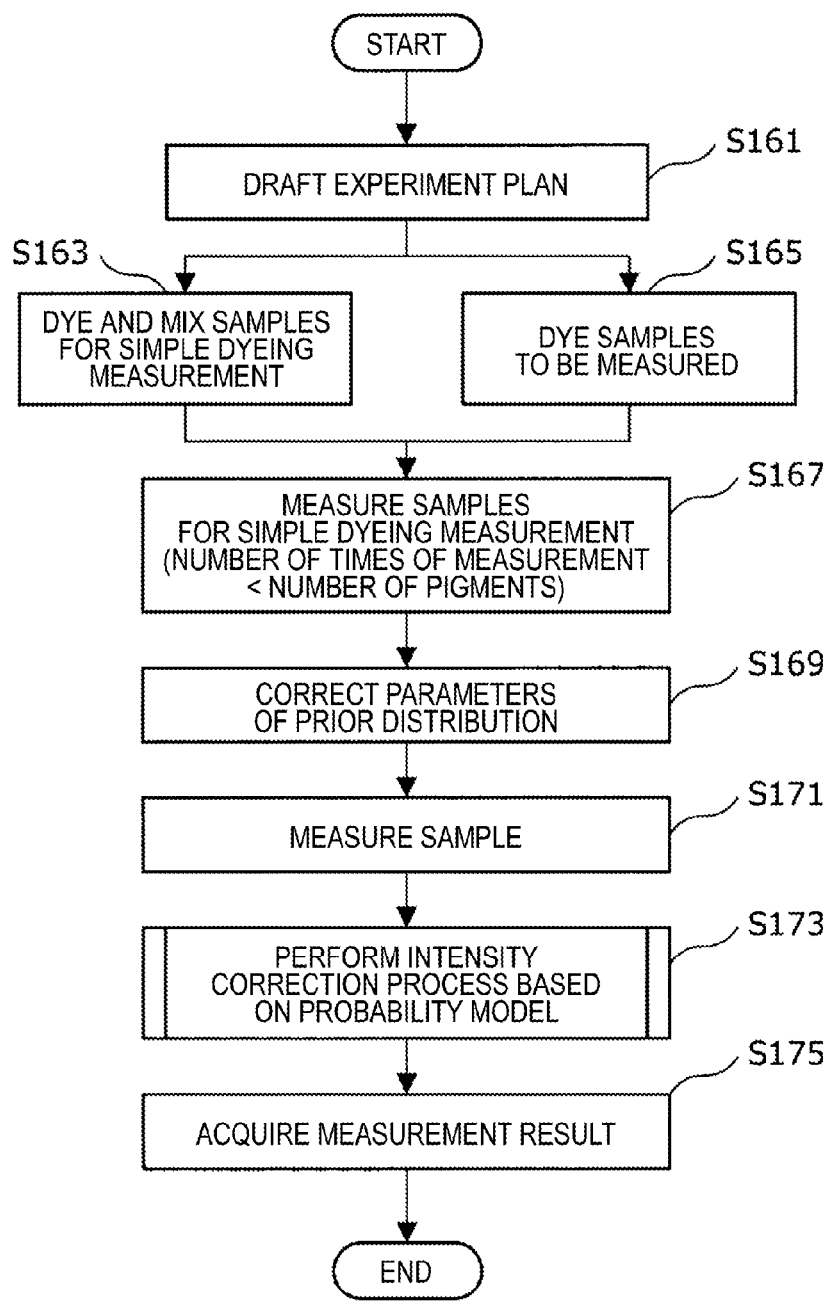
FIG. 14 is a flowchart illustrating an example of the flow of the fluorescence intensity correction process using the information processing method according to the first embodiment.

Next, the flow of the fluorescence intensity correction process using the intensity correction method according to this embodiment will be described with reference to FIGS. 13 to 16. FIGS. 13 and 14 are flowcharts illustrating the flow of the intensity correction process using the intensity correction method according to this embodiment.

First, the flow of the fluorescence intensity correction process will be described with reference to FIG. 13 when the fluorescence spectrum of the simply dyed sample is not measured.

When the intensity correction method according to this embodiment is used, the measurer of the fluorescence spectrum first drafts an experiment plan to perform multi-dyeing on cells to be measured with given fluorescent pigments (step S151) and performs the multi-dyeing on the cells to be measured. Then, the measurer of the fluorescence spectrum measures the fluorescence spectrum of the multi-dyed cells using the flow cytometer shown in FIGS. 6A and 6B (step S153).

The measurer of the fluorescence spectrum transmits the measurement data output from the flow cytometer shown in FIGS. 6A and 6B to the information processing apparatus 10 according to this embodiment, as in FIGS. 8 and 9. The information processing apparatus 10 according to this embodiment performs the intensity correction process based on the above-described probability model based on the databases or the like of the fluorescence characteristics of the fluorescent pigments (step S155) and outputs the obtained result of the intensity correction process. Thus, the measurer of the fluorescence spectrum can acquire the value (that is, the measurement result of the fluorescence spectrum) of the fluorescence intensity originating from each fluorescence pigment (step S157).

In the intensity correction method according to this embodiment, the base vector corresponding to the fluorescence spectrum is corrected based on the measurement result obtained through the measurement of a measurement unit such as a flow cytometer, when each fluorescent pigment is singly used. Therefore, the intensity correction process on which information obtained in the single dyeing of an interest sample such as cells is automatically reflected is performed in accordance with the intensity correction method of this embodiment. Accordingly, the accuracy of the calculated corrected intensity can be improved.

Next, the flow of the measurement of the fluorescence spectrum of the single-dyed sample will be described with reference to FIG. 14.

When the intensity correction method according to this embodiment is used, the measurer of the fluorescence spectrum first drafts an experiment plan to perform multi-dyeing on cells to be measured with given fluorescent pigments (step S161). Then, the measurer of the fluorescent spectrum prepares a mixture sample by mixing several simply dyed samples obtained after samples are dyed for simple dyeing measurement (step S163) and also dyes samples to be measured (step S165).

Thereafter, the measurer of the fluorescence spectrum measures the fluorescence spectrum of the sample using the samples for the simple dyeing measurement prepared in step S163 with the flow cytometer shown in FIGS. 6A and 6B (step S167). At this time, when the intensity correction method according to this embodiment is used, the mixture sample in which several simply dyed samples are mixed can be used. Therefore, the number of times the sample for the simple dyeing measurement is measured can be set to be less than the number of fluorescent pigments to be used in the multiple dyeing of the cells.

When the measurement of the sample for the single dyeing measurement ends, the measurer of the fluorescence spectrum transmits the obtained measurement result of the sample for the simple dyeing measurement to the information processing apparatus 10 according to this embodiment shown in FIGS. 8 and 9. The information processing apparatus 10 according to this embodiment corrects the contents of the parameters of the prior distribution so as to be proper for the interest cells based on the input measurement result before the measurement of the sample (step S169).

After performing the pre-processing described above, the measurer of the fluorescence spectrum measures the fluorescence spectrum of the interest multi-dyed cells using the flow cytometer or the like shown in FIGS. 6A and 6B (step S171). The measurer of the fluorescence spectrum transmits the measurement data output from the flow cytometer used in the measurement to the information processing apparatus 10 according to this embodiment shown in FIGS. 8 and 9.

The information processing apparatus 10 according to this embodiment performs the intensity correction process based on the above-described probability model using the corrected parameters of the prior distribution and the measurement data (step S173) and outputs the obtained result of the intensity correction process. Thus, the measurer of the fluorescence spectrum can acquire the value (that is, the measurement result of the fluorescence spectrum) of the fluorescence intensity originating from each fluorescent pigment (step S175).

Figure 16:
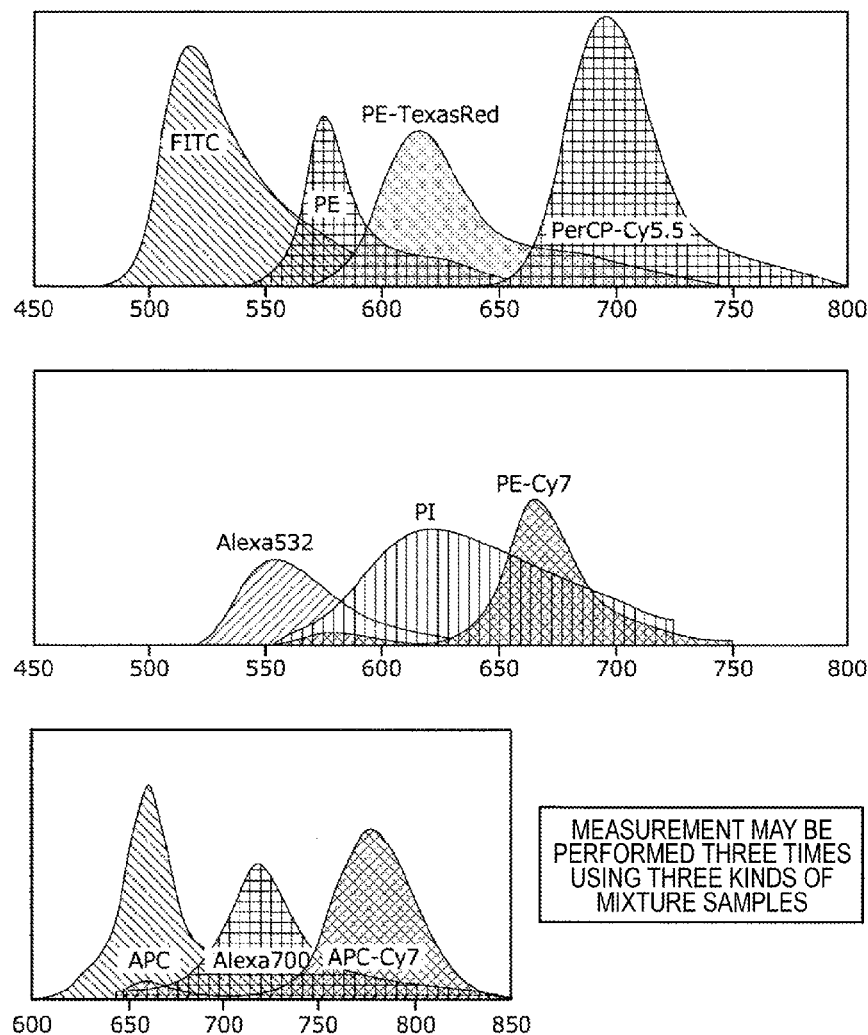
FIG. 16 is a diagram illustrating a base vector generation process using the information processing method according to the first embodiment.

FIGS. 15 and 16 are diagrams illustrating a process of generating the base vectors in accordance with the information processing method of this embodiment.

As shown in FIG. 15, a case in which a sample is multi-dyed using a total of ten kinds of fluorescent pigments of seven kinds of fluorescent pigments excited by a 488 nm laser beam and three kinds of fluorescent pigments excited by a 640 nm laser beam is considered. In particular, there are several peak overlaps indicating the fluorescence characteristics in the seven kinds of fluorescent pigments excited by the 488 nm laser beam, as apparent from FIG. 15.

When the intensity correction method of this embodiment is not used, it is necessary to prepare ten kinds of single-dyed samples using each fluorescent pigment and to perform measurement ten times to generate the base vectors of the ten kinds of fluorescent pigments. However, according to the intensity correction method of this embodiment, the single-dyed spectrum can be measured using a mixture sample so that the number of peak overlaps is small in the fluorescent spectrum to be measured.

Specifically, for example, as shown in FIG. 16, the prior distribution to be used as the base vector can be generated from the actually measured spectrum by preparing three kinds of mixture samples in consideration of a combination of the fluorescent pigments in which the peak wavelengths do not overlap and performing the measurement three times in total. According to the intensity correction method of this embodiment, it is possible to considerably reduce the time or cost necessary for obtaining the measurement result of the single-dyed sample.

The flow of the fluorescent intensity correction process using the intensity correction method according to this embodiment has been described simply above with reference to FIGS. 13 to 16.

(Hardware Configuration)

Figure 17:
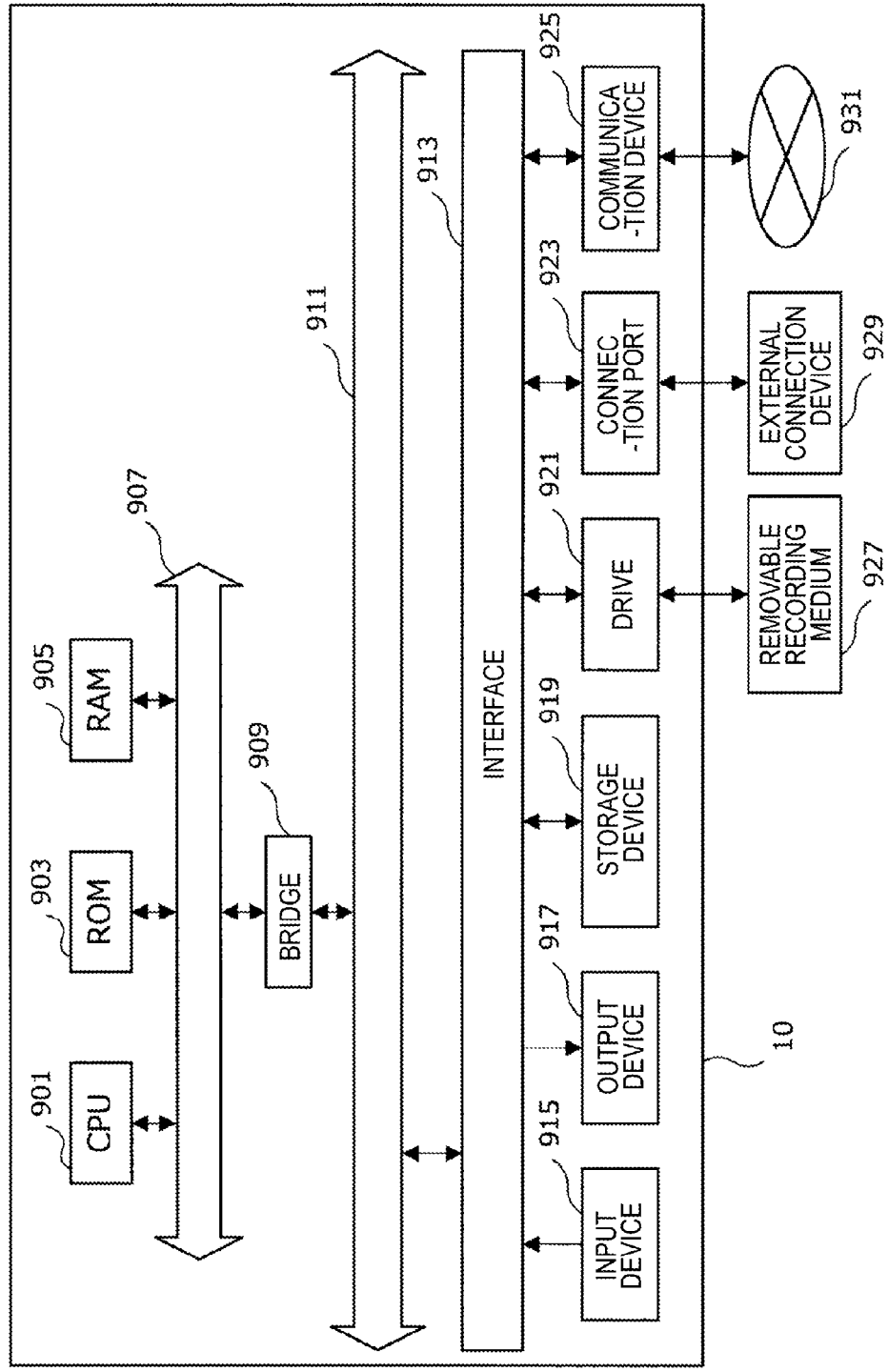
FIG. 17 is a block diagram illustrating a hardware configuration of the information processing apparatus according to an embodiment of the present disclosure.

Next, a hardware configuration of the information processing apparatus 10 according to an embodiment of the present disclosure will be described in detail with reference to FIG. 17. FIG. 17 is a block diagram illustrating the hardware configuration of the information processing apparatus 10 according to the embodiment of the present disclosure.

The information processing apparatus 10 mainly includes a CPU 901, a ROM 903, and a RAM 905. The information processing apparatus 10 further includes a host bus 907, a bridge 909, an external bus 911, an interface 913, an input device 915, an output device 917, a storage device 919, a drive 921, a connection port 923, and a communication device 925.

The CPU 901 serves as an arithmetic processing device and a control device. Thus, the CPU 901 controls all or some of operations of the information processing apparatus 10 in accordance with various programs stored in the ROM 903, the RAM 905, the storage device 919, or a removable recording medium 927. The ROM 903 stores programs, arithmetic parameters, or the like used by the CPU 901. The RAM 905 temporarily stores the programs used by the CPU 901 or parameters or the like appropriately changed in execution of the programs. The CPU, the RAM, and the ROM are connected to each other by a host bus 907 configured by an internal bus such as a CPU bus.

The host bus 907 is connected to an external bus 911 such as a peripheral component interconnect/interface (PCI) bus via the bridge 909.

The input device 915 is an operation unit operated by a user, such as a mouse, a keyboard, a touch panel, a button, a switch, or a lever. For example, the input device 915 may be a remote control unit (so-called remote controller) using infrared rays or other radio waves or may be an external connection device 929 such as a portable telephone or a PDA responding to an operation of the information processing apparatus 10. For example, the input device 915 is configured by an input control circuit or the like that generates an input signal based on information input by the user and outputs the generated input signal to the CPU 901. The user of the information processing apparatus 10 can operate the input device 915 to input various kinds of data or give processing instructions to the information processing apparatus 10.

The output device 917 is configured by a device that is capable of visually or audibly notifying a user of acquired information. Examples of the device include display devices such as CRT display devices, liquid crystal display devices, plasma display devices, EL display devices, or lamps, audio output devices such as speakers and headphones, printer devices, portable telephones, and facsimiles For example, the output device 917 outputs results obtained through various processes of the information processing apparatus 10. Specifically, a display device displays the results obtained through the various processes of the information processing apparatus 10 in the forms of text or images. On the other hand, an audio output device converts an audio signal formed by reproduced audio data or acoustic data into an analog signal and outputs the converted analog signal.

The storage device 919 is a data storing device which is configured as an example of the storage unit of the information processing apparatus 10. The storage device 919 is configured by, for example, a magnetic storage device such as a hard disk drive (HDD), a semiconductor storage device, an optical storage device, or a magneto-optical storage device. The storage device 919 stores the programs or various kinds of data to be executed by the CPU 901 and various kinds of data acquired from the outside.

The drive 921 is a reader and writer for a storage medium and is included in or attached externally to the information processing apparatus 10. The drive 921 reads information stored in the removable recording medium 927 such as a magnetic disk, an optical disc, a magneto-optical disc, or a semiconductor memory mounted on the information processing apparatus and outputs the read information to the RAM 905. Further, the drive 921 can also write information on the removable recording medium 927 such as a magnetic disk, an optical disc, a magneto-optical disc, or a semiconductor memory mounted on the information processing apparatus. Examples of the removable recording medium 927 include a DVD medium, an HD-DVD medium, and a Blu-ray medium. The removable recording medium 927 may be a Compact-Flash (registered trademark) (CF), a flash memory, a secure digital (SD) memory card, or the like. Further, the removable recording medium 927 may be an integrated circuit (IC) card or an electronic apparatus on which a non-contact type IC chip is mounted.

The connection port 923 is a port that directly connects an apparatus to the information processing apparatus 10. Examples of the connection port 923 include a universal serial bus (USB) port, an IEEE1394 port, and a small computer system interface (SCSI) port. Other examples of the connection port 923 include an RS-232C port, an optical audio terminal, and a high-definition multimedia interface (HDMI) port. When the external connection device 929 is connected to the connection port 923, the information processing apparatus 10 directly acquires various kinds of data from the external connection device 929 or provides various kinds of data to the external connection device 929.

For example, the communication device 925 is a communication interface configured by a communication device connected to a communication network 931. Examples of the communication device 925 include a wired or wireless local area network (LAN), Bluetooth (registered trademark), and a communication card for a wireless USB (WUSB). The communication device 925 may be an optical communication router, an asymmetric digital subscriber line (ADSL) router, or modems for various communications. For example, the communication device 925 can transmit or receive a signal or the like to or from the Internet or another communication device in conformity with a predetermined protocol such as TCP/IP. The communication network 931 connected to the communication device 925 is configured by networks connected to each other in a wireless or wired manner. For example, the communication network 931 may be the Internet, a household LAN, infrared communication, radio wave communication, or satellite communication.

An example of the hardware configuration capable of realizing the functions of the information processing apparatus 10 according to the embodiment of the present disclosure has been described above. Each constituent element described above may be configured by a general member or may be configured by hardware specialized in the function of each constituent element. Accordingly, the hardware configuration to be used can be modified appropriately in accordance with a technical level when this embodiment is realized.

Examples

Hereinafter, a technical spirit of the present disclosure will be described in detail according to an example and comparative example. However, the technical spirit of the present disclosure is not limited to the example described below.

In an example described below, usability of the information processing method (intensity correction method) according to the embodiment of the present disclosure was examined using data of the fluorescence spectrum measured when a mixture sample was produced using blood gathered from two different persons and the mixture sample was dyed with three kinds of fluorescent pigments, FITC, Alexa 532, and PE.

Figure 18:
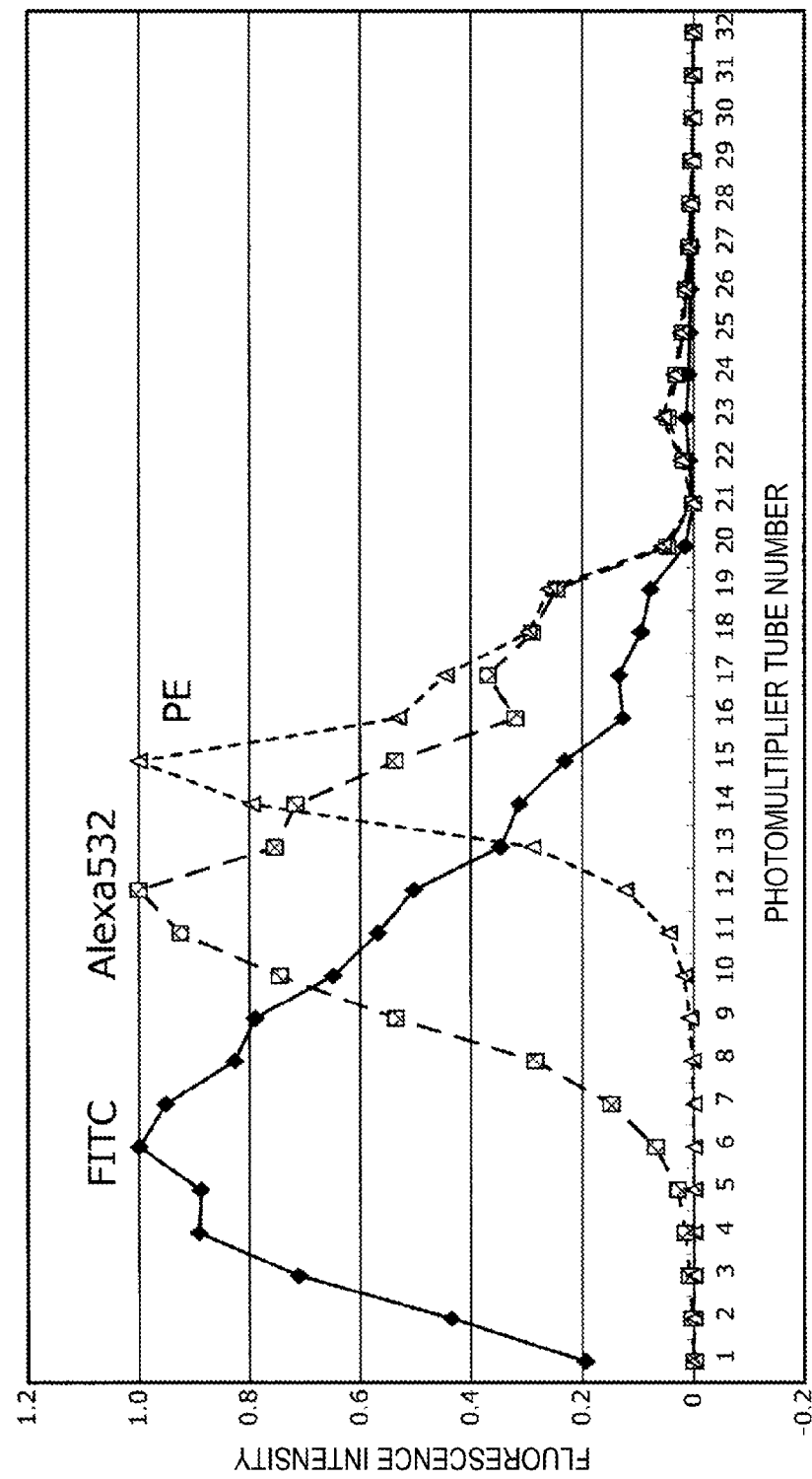
FIG. 18 is a graph illustrating the fluorescence characteristics of fluorescent pigments used to dye a mixture sample.

FIG. 18 is a graph illustrating the fluorescence characteristics of the fluorescent pigments used to dye the mixture sample. The fluorescence characteristics shown in FIG. 18 were measured using the flow cytometer shown in FIGS. 6A and 6B. The horizontal axis of the graph shown in FIG. 18 represents numbers given to the photomultiplier tubes of the flow cytometer used for the measurement, and thus corresponds to the wavelength of the fluorescent spectrum. The vertical axis of the graph represents a fluorescence intensity.

Here, as apparent from the result shown in FIG. 18, it can be understood that peaks indicating the fluorescence characteristics of the three kinds of fluorescent pigments, FITC, Alexa 532, and PE, overlap. Based on the graph shown in FIG. 18, a combination of the three kinds of fluorescent pigments can be said to be a combination of the fluorescent pigments for which calculation of the genuine fluorescence intensity is difficult.

Hereinafter, the usability of the information processing method (intensity correction method) according to the embodiment of the present disclosure was examined by comparing a case in which the base vectors measured by singly dyeing cells were used to a case in which the base vectors measured by singly dyeing latex beads were used. Here, the base vector measured by singly dyeing the cells is referred to as a cell-single dyeing base vector or a cell-single dyeing prior distribution. The base vector measured by singly dyeing the latex beads is referred to as a bead-single dyeing base vector or a bead-single dyeing prior distribution.

Figure 19A:
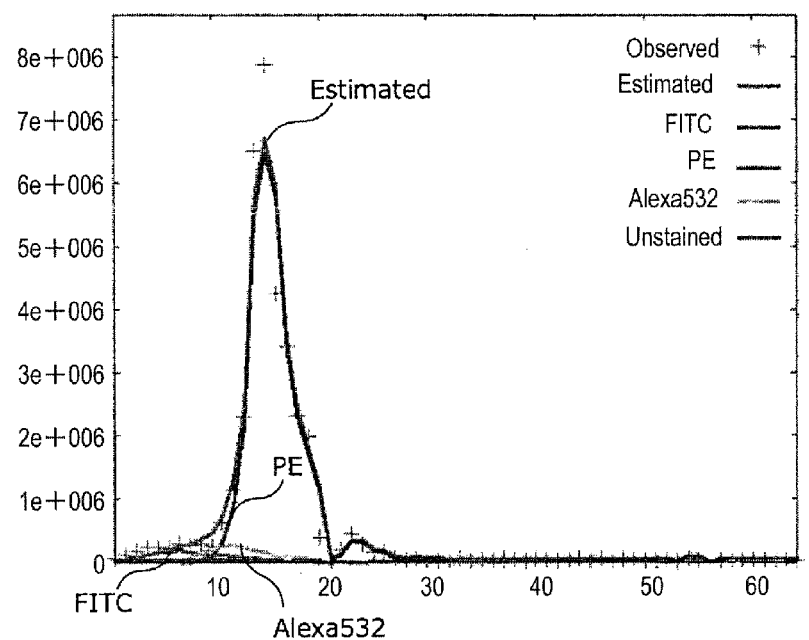
FIG. 19A is a graph illustrating a fitting case of measurement data.
Figure 19B:
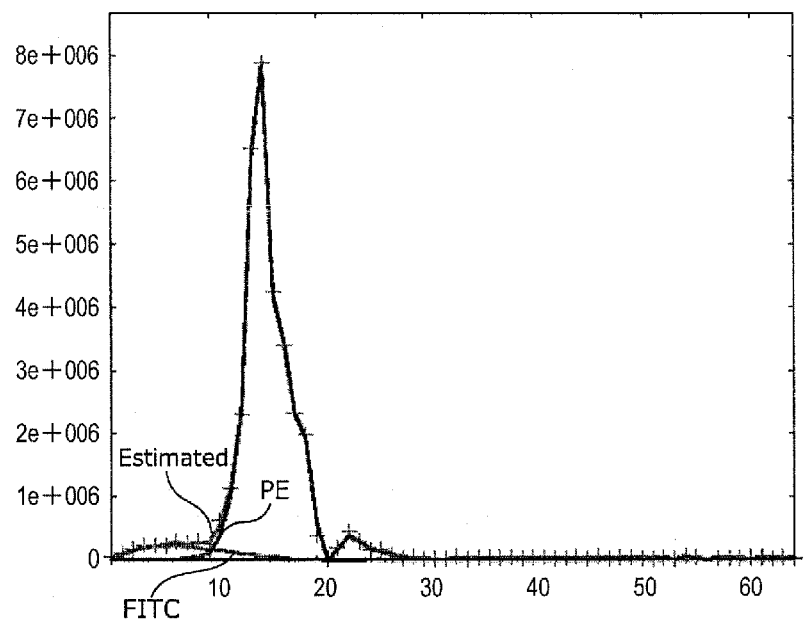
FIG. 19B is a graph illustrating a fitting case of measurement data.
Figure 19C:
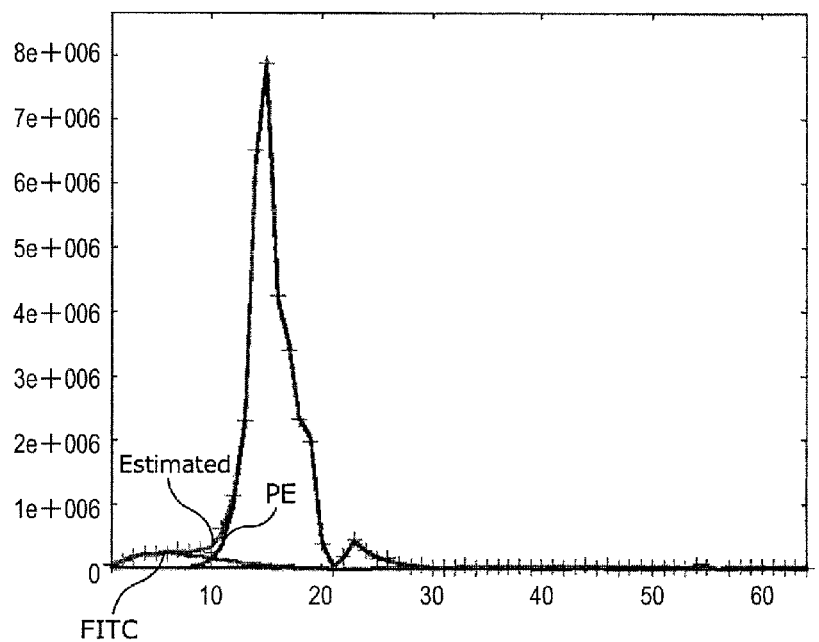
FIG. 19C is a graph illustrating a fitting case of measurement data.

FIGS. 19A to 19C show fitting cases of the measurement results of the fluorescence spectrum measured in the multi-dyeing of the above-mentioned mixture sample using the base vectors.

Figure 3:
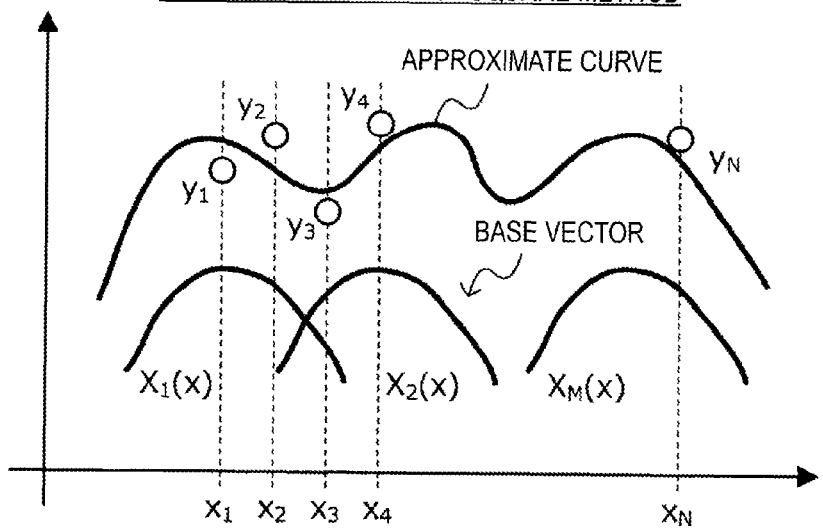
FIG. 3 is a diagram illustrating the fluorescence intensity correction process.

FIG. 19A is a diagram illustrating the fitting case of the measurement data in accordance with the restricted least square method exemplified in FIGS. 3 and 4 using the bead-single dyeing base vector. As apparent from FIG. 19A, it can be understood that the approximate curve (a curve denoted by Estimated in the drawing) obtained by the least square method does not reproduce an actually measured fluorescence spectrum. Further, when the base vectors used to calculate the approximate curve are focused on, the base vector regarding Alexa 532 can be understood to be used in addition to the base vector regarding FITC and the base vector regarding PE.

FIG. 19B is a diagram illustrating the fitting case of the measurement data in accordance with the restricted least square method using the cell-single dyeing base vector. Referring to FIG. 19B, it can be understood that the approximate curve (a curve denoted by Estimated in the drawing) obtained by the least square method reproduces an actually measured fluorescence spectrum. Further, when the base vectors used to calculate the approximate curve are focused on, it can be understood that the base vector regarding FITC and the base vector regarding PE are mainly used and the base vector regarding Alexa 532 is not used.

When FIGS. 19A and 19B are compared to each other, it is apparent that to fit the measurement data by the restricted least square method, the bead-single dyeing base vector is not used, but the cell-single dyeing base vector for which time or cost is necessary to generate the base vector should be used.

FIG. 19C is a diagram illustrating the fitting case of the measurement data in accordance with the fluorescence intensity correction method according to the embodiment of the present disclosure. Referring to FIG. 19C, it can be understood that the approximate curve (a curve denoted by Estimated in the drawing) obtained by the present suggestion method reproduces an actually measured fluorescence spectrum. Further, when the base vectors used to calculate the approximate curve are focused on, it can be understood that the base vector regarding FITC and the base vector regarding PE are mainly used and the base vector regarding Alexa 532 is not used.

According to the present suggestion method, it is possible to obtain the same result as the case in which the cell-single dyeing base vector is used, even when there is a probability that the bead-single dyeing base vector is lower in accuracy than the cell-single base vector.

Figure 20A:
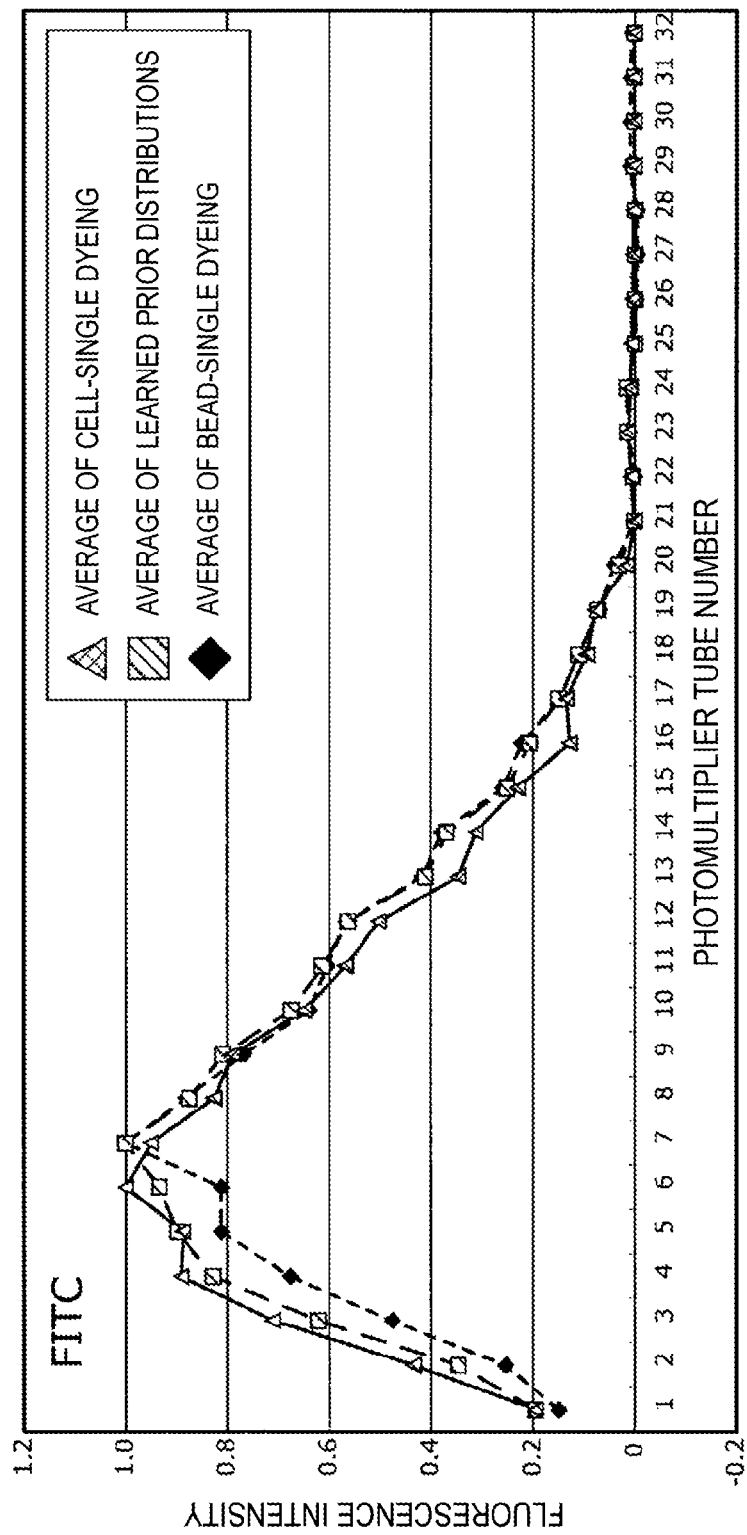
FIG. 20A is a graph illustrating a change in a base vector of a fluorescent pigment FITC.
Figure 20B:
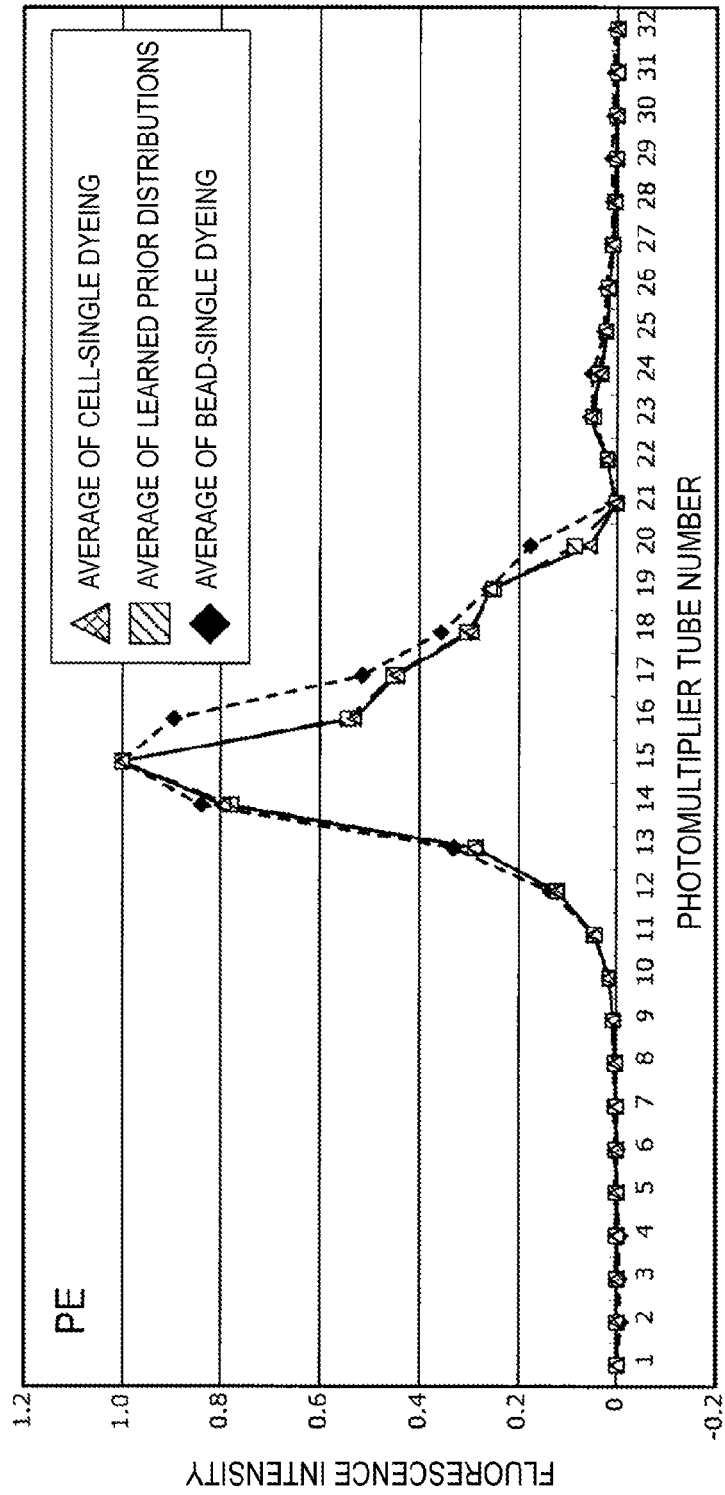
FIG. 20B is a graph illustrating a change in a base vector of a fluorescent pigment PE.

Here, knowledge concerning a change in the base vector of the interest fluorescent pigment, for example, the fluorescent pigments FITC and PE, in the above-described fitting processes is shown in FIGS. 20A and 20B. FIG. 20A is a graph illustrating a change in the base vector of the fluorescent pigment FITC. FIG. 20B is a graph illustrating a change in the base vector of the fluorescent pigment PE.

In FIGS. 20A and 20B, a plot indicated by Δ represents an average of the cell-single dyeing base vectors, a plot indicated by ♦ represents an average of the bead-single dyeing base vectors, and a plot indicated by represents an average of the base vectors (that is, the prior distributions) estimated by the present suggestion method. According to the present suggestion method, the plot indicated by can be understood to be the result when the prior distributions are learned to be suitable for the measurement data so that the parameters indicating the prior distribution are frequently corrected based on the measurement data or the like.

As apparent from FIGS. 20A and 20B, it can be understood that the average of the prior distributions obtained through the learning of the measurement data by the present suggestion method is a distribution very similar to the cell-single dyeing base vector. As apparent from this result, according to the present suggestion method, it can be understood that the result very similar to the cell-single dyeing base vector can be obtained even when the intensity correction process starts using the bead-single dyeing base vector as the initial value so that the prior distributions (base vectors) are learned to be suitable for the measurement data.

Next, two-dimensional correlation diagrams generated using the cell-single dyeing prior distributions according to the restricted least square method and the present suggestion method will be described with reference to FIGS. 21A and 21B. FIGS. 21A and 21B are graphs illustrating two-dimensional correlation diagrams of the mixture sample generated using the cell-single dyeing prior distributions according to the restricted least square method and the present suggestion method. Here, the two-dimensional correlation diagrams shown in FIGS. 21A and 21B are diagrams in which the fluorescence intensities of two kinds of fluorescent pigments selected from three kinds of fluorescent pigments (FITC, Alexa 532, and PE) are plotted on a logarithmic scale.

Referring to FIGS. 21A and 21B, in the two-dimensional correlation diagrams in which the fluorescence intensities of FITC and PE are plotted and the two-dimensional correlation diagrams in which the fluorescence intensities of FITC and Alexa 532 are plotted, it can be understood that very similar groups (populations) are shown in the restricted least square method and the present suggestion method. However, in the two-dimensional correlation diagrams (the correlation diagrams shown on the right side) in which the fluorescence intensities of PE and Alexa 532 are plotted, it can be understood that there is a difference between behaviors of the displayed groups in the restricted least square method and the present suggestion method in areas surrounded by a middle line in the diagrams. More specifically, in the two-dimensional correlation diagram generated according to the restricted least square method, the area surrounded by the middle line in the diagram seems to be a single large group connected in a portion indicated by an arrow in the diagram. Further, in the two-dimensional correlation diagram generated using the present suggestion method, there are two groups in the area surrounded by the middle line in the diagram.

Figure 22A:
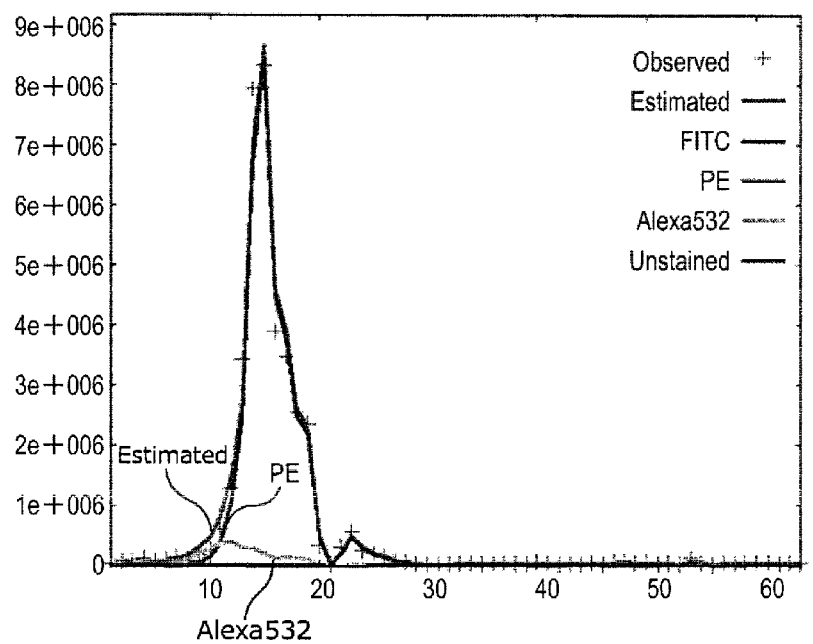
FIG. 22A is a graph illustrating a fitting result of the measurement data according to a restricted least-square method.
Figure 22B:
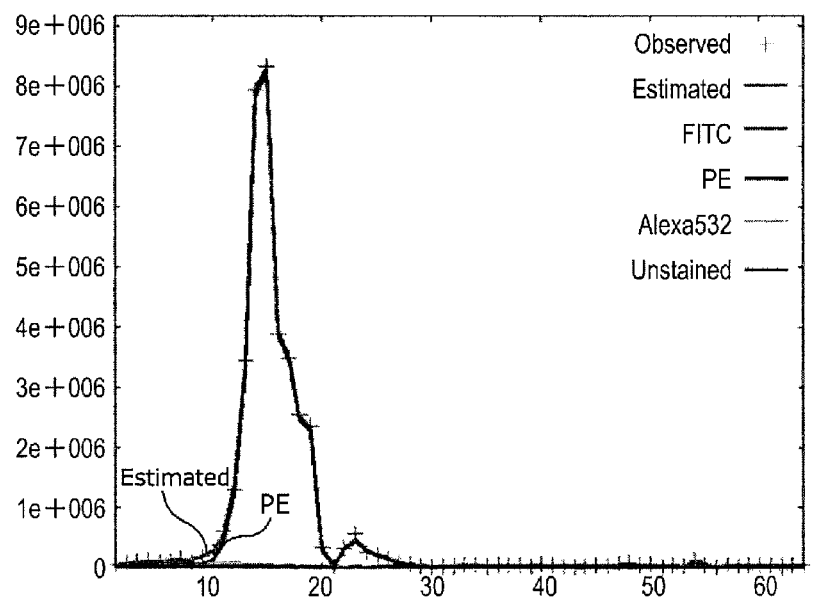
FIG. 22B is a graph illustrating a fitting result of the measurement data when a cell-single dyeing base vector is used.

The fitting result of the portion indicated by the arrow in FIG. 21A is shown in FIG. 22A and the fitting result of the portion indicated by the arrow in FIG. 21B is shown in FIG. 22B. Referring to FIG. 22A, it can be understood that the measurement data of the corresponding portion is fitted using the base vectors of the fluorescent pigments PE and Alexa 532. Thus, since there is room for accuracy of the fitting in which the base vector of the fluorescent pigment PE is used, it is considered that the fluorescence intensity of the fluorescent pigment Alexa 532 may leak into the fluorescence intensity of the fluorescent pigment PE, and thus the single large group shown in FIG. 21A may be formed.

Since a process of estimating the base vector of the fluorescent pigment PE is performed in the fitting result obtained according to the present suggestion method shown in FIG. 22B, the measurement data of the corresponding portion is fitted using the base vector of the fluorescent pigment PE (without using the base vector of the fluorescent pigment Alexa 532). From this viewpoint, it is suggested that the leakage of the fluorescence intensity occurring in the restricted least square method is appropriately corrected and the two groups shown in FIG. 21B are shown in the two-dimensional correlation diagram.

Next, two-dimensional correlation diagrams generated using the bead-single dyeing prior distributions according to the restricted least square method and the present suggestion method will be described with reference to FIGS. 23A and 23B. FIGS. 23A and 23B are graphs illustrating two-dimensional correlation diagrams of the mixture sample generated using the bead-single dyeing prior distributions according to the restricted least square method and the present suggestion method. Here, the two-dimensional correlation diagrams shown in FIGS. 23A and 23B are diagrams in which the fluorescence intensities of two kinds of fluorescent pigments selected from three kinds of fluorescent pigments (FITC, Alexa 532, and PE) are plotted in a logarithmic scale.

In FIGS. 23A and 23B, a plurality of groups estimated from the plotted distributions are segmented in each two-dimensional correlation diagram and the boundaries of the groups are indicated by solid lines. A number written in each area represents the number of plots included in each area and a number written in parentheses represents a difference in the number of plots when the cell-single dyeing prior distributions are used.

As apparent from the two-dimensional correlation diagrams shown on the right side of FIGS. 23A and 23B, it can be understood that the leakage of the fluorescence intensity occurring in the restricted least square method is appropriately corrected according to this suggestion method, even when the bead-single dyeing prior distributions are used. Further, compared to the three kinds of two-dimensional correlation diagrams, the difference in the number of plots with the cell-single dyeing prior distributions is large in the two-dimensional correlation diagrams according to the restricted least square method. According to the present suggestion method, however, the difference in the number with the cell-single dyeing prior distributions is very small. This result shows that the same result as the cell-single dyeing prior distribution can be obtained through the learning of the measurement data from the bead-single dyeing prior distributions in accordance with the intensity correction method conforming to the present suggestion method.

Figure 24:
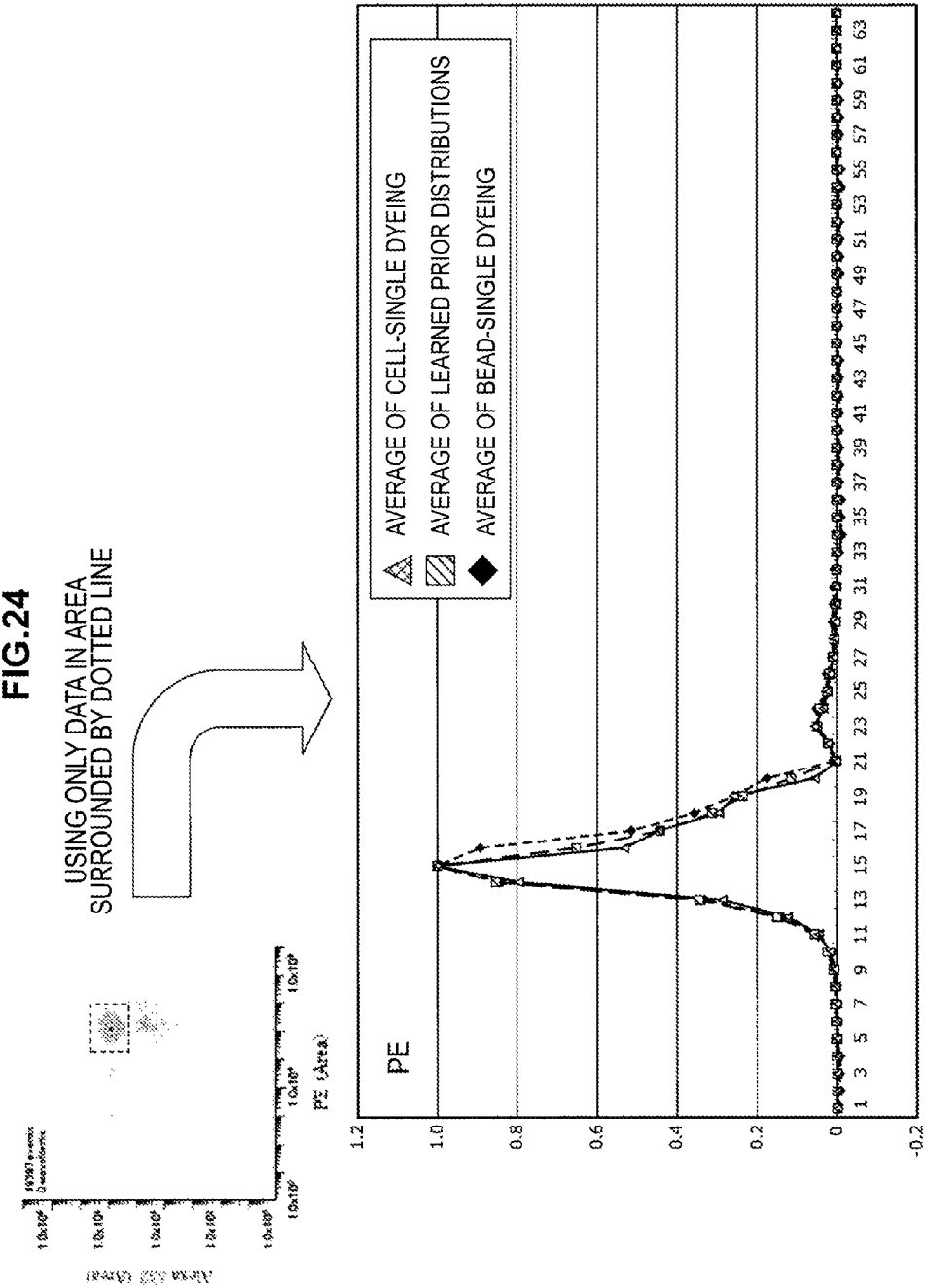
FIG. 24 is a diagram illustrating a learning result of prior distributions using some of the measurement data.

FIG. 24 is a diagram illustrating the learning result of the prior distributions using some of the measurement data. In an example shown in FIG. 24, a result is obtained by verifying whether the prior distributions can appropriately be learned using only the measurement data corresponding to the groups present on the upper right side of the two-dimensional correlation diagram. As apparent from the graph shown in FIG. 24, the average of the prior distributions learned using only the measurement data of the area surrounded by a dotted line is similar to the average of the cell-single dyeing prior distributions rather than the average of the bead-single dyeing prior distributions. This result clarifies that the prior distributions can be appropriately learned even when the learning is performed using only some of the measurement data according to the present suggestion method.

The example in which the intensity correction method according to the embodiment of the present disclosure is used has been described in detail above with reference to FIGS. 18 to 24. As described above, the fluorescence characteristics of the fluorescent pigments are estimated in each measurement in the intensity correction method according to the embodiment of the present disclosure. Therefore, the leakage of the problematic fluorescent intensity can be corrected through the fluorescence correction according to the restricted least square method. Further, in the intensity correction method according to the embodiment of the present disclosure, the prior knowledge (for example, the measurement data or the like of each fluorescent pigment obtained through the prior measurement) concerning the fluorescent characteristics of each fluorescent pigment can be corrected in accordance with the measurement data of the sample. Therefore, even when the prior knowledge for which there is room for accuracy is set as the initial value, the intensity correction result can be obtained with high accuracy.

It should be understood by those skilled in the art that various modifications, combinations, sub-combinations and alterations may occur depending on design requirements and other factors insofar as they are within the scope of the appended claims or the equivalents thereof.

Additionally, the technologies disclosed in the present specification can be expressed as follows, for example.

(1)

An information processing apparatus including:

an estimation unit that expresses a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, models the light intensity distribution obtained from each of the reference measurement objects so as to follow a predetermined probability distribution, and estimates a combination coefficient of the linear combination from the light intensity distribution obtained from the measurement object of the measurement target.

(2)

The information processing apparatus according to (1), wherein the estimation unit determines whether estimated values of the combination coefficient and the light intensity distribution obtained from the measurement object of the measurement target based on the combination coefficient converge, the information processing apparatus further includes a parameter setting control unit that updates a parameter, which defines the predetermined probability distribution, using the estimated values, when the estimation unit determines that the estimated values do not converge, and the estimation unit again estimates the combination coefficient and a parameter, which defines the predetermined probability distribution, using the updated parameter which defines the predetermined probability distribution.

(3)

The information processing apparatus according to (2), wherein the estimation unit models a component other than a light component, which has an influence on the light intensity distribution obtained by irradiating the light to the measurement object of the measurement target and is obtained from the reference measurement object, so as to follow a different predetermined probability distribution and estimates the combination coefficient of the linear combination from the light intensity distribution obtained from the measurement object of the measurement target, and the parameter setting control unit updates the parameter which defines the different predetermined probability distribution using the estimated values when the parameter setting control unit updates the parameter which defines the predetermined probability distribution.

(4)

The information processing apparatus according to (2), wherein the estimation unit uses a light intensity distribution obtained in advance from the reference measurement object as prior knowledge which is used when the light intensity distribution obtained from the reference measurement object is estimated based on the predetermined probability distribution.

(5)

The information processing apparatus according to (2), wherein the parameter setting control unit commonly uses the parameter which is updated using the estimated values calculated by the estimation unit and defines the predetermined probability distribution, even when the light intensity distributions for the measurement objects of a plurality of the measurement targets are measured.

(6)

The information processing apparatus according to (2), wherein the measurement object of the measurement target is microparticles which are multi-dyed using a plurality of fluorescent pigments, and the substance is a fluorescent pigment to be used to dye the microparticles.

(7)

An information processing method including:

expressing a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, modeling the light intensity distribution obtained from each of the reference measurement objects so as to follow a predetermined probability distribution, and estimating a combination coefficient of the linear combination from the light intensity distribution obtained from the measurement object of the measurement target.

(8)

A program for causing a computer to execute a function of:
expressing a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, modeling the light intensity distribution obtained from each reference measurement object so as to follow a predetermined probability distribution, and estimating a combination coefficient of the linear combination from the light intensity distribution obtained from the measurement object of the measurement target.

(9)

A method of correcting an intensity of a fluorescence spectrum, including:
measuring a fluorescence spectrum of microparticles by irradiating light with predetermined wavelength to the microparticles which are multi-dyed with a plurality of fluorescent pigments; and
correcting a fluorescent intensity of the measured fluorescent spectrum of the microparticles based on information regarding fluorescence characteristics of the single fluorescent pigment,
wherein, to correct the fluorescent intensity,
the fluorescence spectrum of the microparticles is treated as a linear sum of multiplications of fluorescence spectra of the fluorescent pigments and predetermined weighting coefficients, and a parameter indicating an intensity distribution corresponding to the fluorescence spectrum of the fluorescent pigment is set based on the information regarding the fluorescence characteristics of the single fluorescent pigment,
a likely weighting coefficient corresponding to the fluorescence spectrum of the microparticles and the parameter indicating the intensity distribution are estimated based on the fluorescent spectrum of the microparticles and the intensity distribution corresponding to the fluorescence spectrum of the fluorescent pigment, and
the estimated weighting coefficient is considered as a fluorescence intensity originating from each fluorescent pigment.

(10)

The method of correcting an intensity of a fluorescence spectrum according to (9), further including:
classifying the plurality of fluorescent pigments into a plurality of groups in which fluorescence peak wavelengths do not overlap, before the measurement of the fluorescence spectrum of the microparticles;
singly dyeing the microparticles with the fluorescent pigment belonging to the corresponding group;
adjusting a mixture sample, in which the single-dyed microparticles are mixed, in each group; and
measuring a fluorescence spectrum of the mixture sample using the adjusted mixture sample;
wherein, to correct the fluorescent intensity, a parameter indicating the intensity distribution corresponding to the fluorescence spectrum of the fluorescent pigment is set using the fluorescence spectrum of each mixture sample.

The present disclosure contains subject matter related to that disclosed in Japanese Priority Patent Application JP2011-161758 filed in the Japan Patent Office on Jul. 25, 2011, the entire content of which is hereby incorporated by reference.

What is claimed is:

1. An information processing apparatus comprising:
an estimation unit that expresses a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, models the light intensity distribution obtained from each of the reference measurement objects so as to follow a predetermined probability distribution, and estimates a combination coefficient of the linear combination from the light intensity distribution obtained from the measurement object of the measurement target.

2. The information processing apparatus according to claim 1,
wherein the estimation unit determines whether estimated values of the combination coefficient and the light intensity distribution obtained from the measurement object of the measurement target based on the combination coefficient converge,
the information processing apparatus further includes a parameter setting control unit that updates a parameter, which defines the predetermined probability distribution, using the estimated values, when the estimation unit determines that the estimated values do not converge, and
the estimation unit again estimates the combination coefficient and a parameter, which defines the predetermined probability distribution, using the updated parameter which defines the predetermined probability distribution.

3. The information processing apparatus according to claim 2,
wherein the estimation unit models a component other than a light component, which has an influence on the light intensity distribution obtained by irradiating the light to the measurement object of the measurement target and is obtained from the reference measurement object, so as to follow a different predetermined probability distribution and estimates the combination coefficient of the linear combination from the light intensity distribution obtained from the measurement object of the measurement target, and
the parameter setting control unit updates the parameter which defines the different predetermined probability distribution using the estimated values when the parameter setting control unit updates the parameter which defines the predetermined probability distribution.

4. The information processing apparatus according to claim 2,
wherein the estimation unit uses a light intensity distribution obtained in advance from the reference measurement object as prior knowledge which is used when the light intensity distribution obtained from the reference measurement object is estimated based on the predetermined probability distribution.

5. The information processing apparatus according to claim 2,
wherein the parameter setting control unit commonly uses the parameter which is updated using the estimated values calculated by the estimation unit and defines the predetermined probability distribution, even when the light intensity distributions for the measurement objects of a plurality of the measurement targets are measured.

6. The information processing apparatus according to claim 2,
wherein the measurement object of the measurement target is microparticles which are multi-dyed using a plurality of fluorescent pigments, and
the substance is a fluorescent pigment to be used to dye the microparticles.

7. An information processing method comprising:
expressing a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance, modeling the light intensity distribution obtained from each of the reference measurement objects so as to follow a predetermined probability distribution, and estimating a combination coefficient of the linear combination from the light intensity distribution obtained from the measurement object of the measurement target.

8. A computer-readable recording medium having recorded thereon a program for causing a control unit of the computer-readable recording medium to execute a function of:
expressing a light intensity distribution, which is obtained by irradiating light to a measurement object of a measurement target having a plurality of substances with mutually different responsive characteristics to the light on a surface and/or an inside of the measurement object, as a linear combination of light intensity distributions, which are obtained by irradiating the light to reference measurement objects, each of which has a single substance,
modeling the light intensity distribution obtained from each reference measurement object so as to follow a predetermined probability distribution, and
estimating a combination coefficient of the linear combination from the light intensity distribution obtained from the measurement object of the measurement target.

9. A method of correcting an intensity of a fluorescence spectrum, comprising:
measuring a fluorescence spectrum of microparticles by irradiating light with predetermined wavelength to the microparticles which are multi-dyed with a plurality of fluorescent pigments; and
correcting a fluorescent intensity of the measured fluorescent spectrum of the microparticles based on information regarding fluorescence characteristics of the single fluorescent pigment,
wherein, to correct the fluorescent intensity,
the fluorescence spectrum of the microparticles is treated as a linear sum of multiplications of fluorescence spectra of the fluorescent pigments and predetermined weighting coefficients, and a parameter indicating an intensity distribution corresponding to the fluorescence spectrum of the fluorescent pigment is set based on the information regarding the fluorescence characteristics of the single fluorescent pigment,
a likely weighting coefficient corresponding to the fluorescence spectrum of the microparticles and the parameter indicating the intensity distribution are estimated based on the fluorescent spectrum of the microparticles and the intensity distribution corresponding to the fluorescence spectrum of the fluorescent pigment, and
the estimated weighting coefficient is considered as a fluorescence intensity originating from each fluorescent pigment.

10. The method of correcting an intensity of a fluorescence spectrum according to claim 9, further comprising:
classifying the plurality of fluorescent pigments into a plurality of groups in which fluorescence peak wavelengths do not overlap, before the measurement of the fluorescence spectrum of the microparticles;
singly dyeing the microparticles with the fluorescent pigment belonging to the corresponding group;
adjusting a mixture sample, in which the single-dyed microparticles are mixed, in each group; and
measuring a fluorescence spectrum of the mixture sample using the adjusted mixture sample;
wherein, to correct the fluorescence intensity, a parameter indicating the intensity distribution corresponding to the fluorescence spectrum of the fluorescent pigment is set using the fluorescence spectrum of each mixture sample.

* * * * *